(12) United States Patent
Ferrante et al.

(10) Patent No.: US 11,033,666 B2
(45) Date of Patent: Jun. 15, 2021

(54) PERCUTANEOUS GAS DIFFUSION DEVICE SUITABLE FOR USE WITH A SUBCUTANEOUS IMPLANT

(71) Applicant: Giner, Inc., Newton, MA (US)

(72) Inventors: Anthony A. Ferrante, Belmont, MA (US); Simon G. Stone, Arlington, MA (US)

(73) Assignee: GINER LIFE SCIENCES, INC., Newton, MA (US)

( * ) Notice: Subject to any disclaimer, the term of this patent is extended or adjusted under 35 U.S.C. 154(b) by 179 days.

(21) Appl. No.: 15/814,298

(22) Filed: Nov. 15, 2017

(65) Prior Publication Data

US 2018/0133383 A1    May 17, 2018

Related U.S. Application Data

(60) Provisional application No. 62/422,397, filed on Nov. 15, 2016.

(51) Int. Cl.
*A61M 1/16* (2006.01)
*C25B 1/04* (2021.01)
(Continued)

(52) U.S. Cl.
CPC .......... *A61M 1/16* (2013.01); *A61M 39/0247* (2013.01); *A61N 1/0504* (2013.01);
(Continued)

(58) Field of Classification Search
CPC ............... A61M 1/16; A61M 39/0247; A61M 2205/7536; A61M 2202/0208;
(Continued)

(56) References Cited

U.S. PATENT DOCUMENTS 150,995 A    5/1874  Zwietusch
3,005,943 A    10/1961 Jaffe
(Continued)

FOREIGN PATENT DOCUMENTS

CA    2112952 A1    6/1995
CN    1036511 A    10/1989
(Continued)

OTHER PUBLICATIONS

Suzuki et al., "Number and Volume of Islets Transplanted in Immunobarrier Devices," Cell Transplantation, 7(1):47-52 (1998).
(Continued)

*Primary Examiner* — Nathan R Price
*Assistant Examiner* — Dung T Ulsh
(74) *Attorney, Agent, or Firm* — Kriegsman & Kriegsman

(57) ABSTRACT

Percutaneous gas diffusion device. In one embodiment, the percutaneous gas diffusion device includes a core layer, an outer layer, and an intermediate layer. The core layer may be cylindrical and may include a gas-permeable, liquid-impermeable material. The outer layer may peripherally surround the core layer and may include a tissue-integrating material. The intermediate layer may peripherally surround the core layer and may be peripherally surrounded by the outer layer. The intermediate layer may include a barrier that prevents infiltration of tissue from the outer layer into the core layer and that additionally reduces diffusion of gas from the core layer into the outer layer. The percutaneous gas diffusion device may be coupled to a subcutaneous implant device, such as a subcutaneous container holding implanted cells and/or tissue, a subcutaneous electrochemical oxygen concentrator, or a water electrolyzer.

36 Claims, 15 Drawing Sheets

(51) Int. Cl.
*C25B 9/73* (2021.01)
*A61M 39/02* (2006.01)
*A61N 1/05* (2006.01)
*A61F 2/30* (2006.01)
*A61L 27/54* (2006.01)
*H01M 8/16* (2006.01)

(52) U.S. Cl.
CPC .................. *C25B 1/04* (2013.01); *C25B 9/73* (2021.01); *A61B 2217/002* (2013.01); *A61F 2/30767* (2013.01); *A61L 27/54* (2013.01); *H01M 8/16* (2013.01)

(58) Field of Classification Search
CPC .. A61M 5/14276; A61N 1/0504; A61F 2/022; A61F 2013/00855; A61F 2013/00572; A61F 2013/00246
See application file for complete search history.

(56) References Cited

U.S. PATENT DOCUMENTS

| | | | |
|---|---|---|---|
| 3,373,057 A | 3/1968 | Jost et al. | |
| 3,453,086 A | 7/1969 | Harm | |
| 3,783,868 A * | 1/1974 | Bokros | A61N 1/05 604/891.1 |
| 3,933,526 A | 1/1976 | Rackin | |
| 4,057,479 A | 11/1977 | Campbell | |
| 4,385,093 A | 5/1983 | Hubis | |
| 4,648,391 A | 3/1987 | Ellis | |
| 4,853,223 A | 8/1989 | Graf et al. | |
| 4,925,732 A | 5/1990 | Driskill et al. | |
| 5,011,472 A | 4/1991 | Aebischer et al. | |
| 5,026,615 A | 6/1991 | Tucholski | |
| 5,264,276 A | 11/1993 | McGregor et al. | |
| 5,338,662 A | 8/1994 | Sadri | |
| 5,344,454 A | 9/1994 | Clarke et al. | |
| 5,356,771 A | 10/1994 | O'Dell | |
| 5,362,622 A | 11/1994 | O'Dell et al. | |
| 5,385,821 A | 1/1995 | O'Dell et al. | |
| 5,586,438 A | 12/1996 | Fahy | |
| 5,713,888 A | 2/1998 | Neuenfeldt et al. | |
| 5,782,912 A | 7/1998 | Brauker et al. | |
| 5,788,682 A | 8/1998 | Maget | |
| 5,902,745 A | 5/1999 | Butler et al. | |
| 5,951,538 A | 9/1999 | Joshi et al. | |
| 5,965,433 A | 10/1999 | Gardetto et al. | |
| 6,060,640 A | 5/2000 | Pauley et al. | |
| 6,171,368 B1 | 1/2001 | Maget et al. | |
| D453,828 S | 2/2002 | Brassil et al. | |
| 6,368,592 B1 | 4/2002 | Colton et al. | |
| 6,455,518 B2 | 9/2002 | Zenke et al. | |
| 6,475,716 B1 | 11/2002 | Seki | |
| 6,492,103 B1 | 12/2002 | Taylor | |
| 6,673,594 B1 | 1/2004 | Owen et al. | |
| 6,677,150 B2 | 1/2004 | Alford et al. | |
| 6,686,197 B2 | 2/2004 | Pipeleers | |
| 6,773,458 B1 | 8/2004 | Brauker et al. | |
| 6,824,915 B1 | 11/2004 | Pedicini | |
| 6,977,140 B1 | 12/2005 | Owen et al. | |
| 6,994,954 B2 | 2/2006 | Taylor | |
| 7,176,015 B2 | 2/2007 | Alford et al. | |
| 7,572,622 B2 | 8/2009 | Hassanein et al. | |
| 7,651,835 B2 | 1/2010 | Hassanein et al. | |
| 7,892,222 B2 | 2/2011 | Vardi et al. | |
| 7,947,094 B2 | 5/2011 | Fiebig | |
| 8,012,500 B2 | 9/2011 | Rotem et al. | |
| 8,043,271 B2 | 10/2011 | Stern et al. | |
| 8,083,821 B2 | 12/2011 | Tempelman et al. | |
| 8,088,969 B2 | 1/2012 | Elliott et al. | |
| 8,100,672 B2 | 1/2012 | Walavalkar et al. | |
| 8,110,283 B2 | 2/2012 | Bansal et al. | |
| 8,257,640 B2 | 9/2012 | Anneaux et al. | |
| 8,298,813 B2 | 10/2012 | Holman et al. | |
| 8,349,151 B2 * | 1/2013 | Schmitt | C25B 9/70 204/257 |
| 8,435,520 B2 | 5/2013 | Schuurman et al. | |
| 8,647,393 B2 | 2/2014 | Marshall et al. | |
| 8,900,763 B2 | 12/2014 | Lundblad et al. | |
| 9,357,764 B2 | 6/2016 | Tempelman et al. | |
| 9,433,557 B2 | 9/2016 | Green et al. | |
| 10,266,808 B2 | 4/2019 | Kelly et al. | |
| 10,272,179 B2 | 4/2019 | Martinson et al. | |
| 10,278,372 B2 | 5/2019 | Hering et al. | |
| 2002/0033333 A1 | 3/2002 | Riecke | |
| 2003/0008192 A1 | 1/2003 | Freund et al. | |
| 2003/0031652 A1 | 2/2003 | Hering et al. | |
| 2003/0087427 A1 | 5/2003 | Colton et al. | |
| 2003/0099622 A1 | 5/2003 | Hering et al. | |
| 2003/0170239 A1 | 9/2003 | Hering et al. | |
| 2004/0058432 A1 | 3/2004 | Owen et al. | |
| 2004/0213768 A1 | 10/2004 | Elliott et al. | |
| 2005/0074657 A1 | 4/2005 | Rusta-Sallehy et al. | |
| 2005/0136092 A1 | 6/2005 | Rotem et al. | |
| 2005/0221269 A1 | 10/2005 | Taylor et al. | |
| 2005/0267325 A1 | 12/2005 | Bouchier et al. | |
| 2006/0160204 A1 | 7/2006 | Hassanein et al. | |
| 2006/0178648 A1 * | 8/2006 | Barron | A61M 39/0208 604/288.02 |
| 2006/0292544 A1 | 12/2006 | Hassanein et al. | |
| 2008/0119909 A1 | 5/2008 | Skinner et al. | |
| 2008/0187901 A1 | 8/2008 | Doorschodt et al. | |
| 2008/0226750 A1 | 9/2008 | Roth et al. | |
| 2008/0248350 A1 | 10/2008 | Little et al. | |
| 2008/0281412 A1 | 11/2008 | Smith et al. | |
| 2009/0012502 A1 | 1/2009 | Rotem et al. | |
| 2009/0042072 A1 | 2/2009 | Vu et al. | |
| 2009/0112170 A1 | 4/2009 | Wells et al. | |
| 2009/0197240 A1 | 8/2009 | Fishman et al. | |
| 2010/0108534 A1 * | 5/2010 | Carlstrom, Jr. | F16K 7/17 205/334 |
| 2010/0130916 A1 * | 5/2010 | Stern | A61F 2/022 604/23 |
| 2010/0196439 A1 | 8/2010 | Beck et al. | |
| 2010/0204683 A1 | 8/2010 | Bodor et al. | |
| 2010/0217244 A1 * | 8/2010 | Mann | A61M 39/0247 604/891.1 |
| 2010/0330547 A1 | 12/2010 | Tempelman et al. | |
| 2011/0008886 A1 | 1/2011 | Hering et al. | |
| 2011/0054387 A1 * | 3/2011 | Stern | A61M 39/0208 604/23 |
| 2011/0180064 A1 * | 7/2011 | Tanaka | A61M 25/04 128/200.24 |
| 2011/0212431 A1 | 9/2011 | Bunegin et al. | |
| 2011/0226686 A1 | 9/2011 | Maurer | |
| 2011/0282444 A1 | 11/2011 | Liu et al. | |
| 2011/0295241 A1 | 12/2011 | Ziaie et al. | |
| 2013/0040223 A1 * | 2/2013 | Tsukamoto | H01M 8/0265 429/490 |
| 2013/0096503 A1 * | 4/2013 | Haase | A61M 5/14276 604/152 |
| 2013/0264218 A1 * | 10/2013 | Vinton | C01B 5/00 205/628 |
| 2014/0017304 A1 | 1/2014 | Bosmans et al. | |
| 2014/0187574 A1 | 7/2014 | Schuler et al. | |
| 2014/0249375 A1 * | 9/2014 | Rodrigues, Jr. | A61B 17/3423 600/227 |
| 2014/0257515 A1 | 9/2014 | So et al. | |
| 2014/0343500 A1 * | 11/2014 | Fielder | A61M 39/0247 604/175 |
| 2015/0112247 A1 * | 4/2015 | Tempelman | A61F 2/022 604/26 |
| 2015/0164990 A1 | 6/2015 | Geaney et al. | |
| 2015/0250942 A1 * | 9/2015 | Momose | A61M 5/14228 604/152 |
| 2016/0228377 A1 | 8/2016 | Bomans et al. | |
| 2016/0274087 A1 | 9/2016 | Assefa et al. | |
| 2016/0361365 A1 | 12/2016 | Lee et al. | |
| 2017/0021090 A1 * | 1/2017 | Stroup | A61M 5/165 |
| 2018/0135948 A1 | 5/2018 | Stone et al. | |
| 2018/0318566 A1 | 11/2018 | Ferrante et al. | |
| 2018/0340146 A1 | 11/2018 | Ferber | |
| 2019/0119462 A1 | 4/2019 | Desai et al. | |
| 2019/0125668 A1 | 5/2019 | Fox et al. | |

(56) References Cited

U.S. PATENT DOCUMENTS

| | | | |
|---|---|---|---|
| 2019/0125937 A1 | 5/2019 | Rotem et al. |
| 2019/0134097 A1 | 5/2019 | Ferber |
| 2019/0343615 A1 | 11/2019 | Dalton et al. |

FOREIGN PATENT DOCUMENTS

| | | |
|---|---|---|
| CN | 101569559 A | 11/2009 |
| EP | 0470726 A1 | 2/1992 |
| ES | 2003479 A6 | 11/1988 |
| JP | H07196401 A | 8/1995 |
| JP | 2008519830 A | 6/2008 |
| WO | 9404169 A1 | 3/1994 |
| WO | 9742953 A1 | 11/1997 |
| WO | 0121234 A1 | 3/2001 |
| WO | 0150983 A1 | 7/2001 |
| WO | 2006112720 A2 | 10/2006 |
| WO | 2006122169 A2 | 11/2006 |
| WO | 2008079997 A2 | 7/2008 |
| WO | 2009031154 A2 | 3/2009 |
| WO | 2009094236 A1 | 7/2009 |
| WO | 2010049996 A1 | 5/2010 |
| WO | 2011159246 A1 | 12/2011 |
| WO | 2014171842 A1 | 10/2014 |
| WO | 2017218714 A1 | 12/2017 |
| WO | 2018085714 A1 | 5/2018 |
| WO | 2018102077 A2 | 6/2018 |
| WO | 2018144098 A1 | 8/2018 |
| WO | 2018144099 A1 | 8/2018 |
| WO | 2018207179 A1 | 11/2018 |
| WO | 2018220621 A2 | 12/2018 |
| WO | 2018220622 A2 | 12/2018 |
| WO | 2018220623 A1 | 12/2018 |
| WO | 2019067766 A1 | 4/2019 |
| WO | 2019089943 A1 | 5/2019 |
| WO | 2019089993 A1 | 5/2019 |
| WO | 2019241562 A1 | 12/2019 |

OTHER PUBLICATIONS

Bruin et al., "Maturation and function of human embryonic stem cell-derived pancreatic progenitors in macroencapsulation devices following transplant into mice," Diabetologia, 56:1987-1998 (2013).
Motte et al., "Composition and function of macroencapsulated human embryonic stem cell-derived implants: comparison with clinical human islet cell grafts," Am J Physiol Endocrinal Metab, 307:E838-E846 (2014).
Yanay et al., "Long-Term Erythropoietin Gene Expression from Transduced Cells in Bioisolator Devices," Human Gene Therapy, 14:1587-1593 (2003).
Bartholomew et al., "Baboon Mesenchymal Stem Cells Can Be Genetically Modified to Secrete Human Erythropoietin In Vivo," Human Gene Therapy, 12:1527-1541 (2001).
Sweet et al., "Treatment of diabetic rats with encapsulated islets," J. Cell. Mol. Med., 12(6B):2644-2650 (2008).
Sorenby et al., "Macroencapsulation Protects Against Sensitization after Allogenic Islet Transplantation in Rats," Transplantation, 82(3):393-397 (2006).
Colton, "Implantable Biohybrid Artificial Organs," Cell Transplantation, 4(4): 415-436 (1995).
Moralejo et al., "Sustained glucagon-like peptide 1 expression from encapsulated transduced cells to treat obese diabetic rats," Journal of Bioscience and Bioengineering, 111(4):383-387 (2011).
Chou et al., "Treatment of osteoporosis with TheraCyte-encapsulated parathyroid cells: a study in a rat model," Osteoporos Int, 17:936-941 (2006).
McQuilling et al., "Methods for Incorporating Oxygen-Generating Biomaterials into Cell Culture and Microcapsule Systems," Methods Mol. Biol., 1479:135-141 (2017).
Marshall et al., "Dermal Integration Cuff Improves Resistance to Exit Site Infections in Porcine Bacterial Challenge," Abstract 072, Society for Biomaterials (2011).
Fukano et al., "Epidermal and dermal integration into sphere-templated porous poly(2-hydroxyethyl methacrylate) implants in mice," J Biomed Mater Res A, 94(4):1172-1186 (2010).
International Search Report dated Feb. 7, 2018, in PCT Application No. PCT/US17/61878, the corresponding PCT application to the present application.
Written Opinion dated Feb. 7, 2018, in PCT Application No. PCT/US17/61878, the corresponding PCT application to the present application.
"Gore Technologies" (Gore) Nov. 12, 2016 (Nov. 12, 2016) [online] retrieved from <URL:https://web.archive.org/web/20161112003850/https://www.gore.com/about/technologies>.
Tibell et al., "Survival of Macroencapsulated Allogenic Parathyroid Tissue One Year After Transplantation in Nonimmunosuppressed Humans," Cell Transplantation, 10:591-9 (2001).
Pedraza et al., "Preventing hypoxia-induced cell death in beta cells and islets via hydrolytically activated, oxygen-generating biomaterials," PNAS, 109(11):4245-4250 (2012).
Ludwig et al., "Improvement of islet function in a bioartificial pancreas by enhanced oxygen supply and growth hormone releasing hormone agonist," PNAS, 109(13):5022-5027 (2012).
Tarantal et al., "Real-time Bioluminescence Imaging of Macroencapsulated Fibroblasts Reveals Allograft Protection in Rhesus Monkeys (*Macaca mulatta*)," Transplantation, 88(1):38-41 (2009).
Colton, "Oxygen supply to encapsulated therapeutic cells," Advanced Drug Delivery Reviews, 67-68:93-110 (Feb. 27, 2014).
Weir, "Islet encapsulation: advances and obstacles," Diabetologia, 56:1458-1461 (Apr. 30, 2013).
Ludwig et al., "Transplantation of human islets without immunosuppression," PNAS, 110(47):19054-19058 (Nov. 19, 2013).
Ohsawa et al., "Hydrogen acts as a therapeutic antioxidant by selectively reducing cytotoxic oxygen radicals," Nature Medicine, 13(6):688-694 (2007).
Burns et al., "The Survival of Mammalian Tissues Perfused with Intravascular Gas Mixtures of Oxygen and Carbon Dioxide," Can. J. Biochem. Physiol., 36:499-504 (1958).
Neufeld et al., "The Efficacy of an Immunoisolating Membrane System for Islet Xenotransplantation in Minipigs," PLoS One, 8(8):e70150 (pp. 1-13) (Aug. 1, 2013).
Wood et al., "The hydrogen highway to reperfusion therapy," Nature Medicine, 13(6):673-674 (2007).
Saad et al., "Extension of Ischemic Tolerance of Porcine Livers by Cold Preservation Including Postconditioning with Gaseous Oxygen," Transplantation, 71:498-502 (2001).
Kin et al., "Islet Isolation and Transplantation Outcomes of Pancreas Preserved with University of Wisconsin Solution Versus Two-Layer Method Using Preoxygenated Perfluorocarbon," Transplantation, 82(10):1286-1290 (2006).
Sudan et al., "A New Technique for Combined Liver/Small Intestinal Transplantation," Transplantation, 72 (11):1846-1848 (2001).
Kuhn-Regnier et al., "Coronary oxygen persufflation combined with HTK cardioplegia prolongs the preservation time in heart transplantation," European Journal of Cardio-thoracic Surgery, 17:71-76 (2000).
Hunt et al., "Cannulation of the portal vein for cytotoxic liver perfusion in colorectal carcinomas: an alternative approach," Annals of the Royal College of Surgeons of England, 68:36-38 (1986).
Wu et al., "In Situ Electrochemical Oxygen Generation with an Immunoisolation Device," Ann. N.Y. Acad. Sci., pp. 105-125 (1999).
Moers et al., "Machine Perfusion or Cold Storage in Deceased-Donor Kidney Transplantation," N. Eng. J. Med., 360:7-19 (2009).
Emamaullee et al., "Caspase Inhibitor Therapy Synergizes With Costimulation Blockade to Promote Indefinite Islet Allograft Survival," Diabetes, 59:1469-77 (2010).
Emamaullee et al., "The Caspase Selective Inhibitor EP1013 Augments Human Islet Graft Function and Longevity in Marginal Mass Islet Transplantation in Mice," Diabetes, 57:1556-66 (2008).
Expanding Transplantation Possibilities, Lifeline Scientific Annual Report 2010, Lifeline Scientific, Inc., Itasca, Illinois.
Calhoon et al., "Twelve-Hour Canine Heart Preservation With a Simple, Portable Hypothermic Organ Perfusion Device," Ann. Thorac. Surg., 62:91-3 (1996).

(56) References Cited

OTHER PUBLICATIONS

Hassanein et al., "Continuous Perfusion of Donor Hearts in the Beating State Extends Preservation Time and Improves Recovery of Function," J. Thorac. Cardiovasc. Surg., 116:821-30 (1998).

Weegman et al., "Continuous Real-Time Viability Assessment of Kidneys Based on Oxygen Consumption," Transplant Proc., 42(6):2020-2023 (2010).doi:10.1016/j.transproceed.2010.05.082.

Suszynski et al., "Persufflation (or gaseous oxygen perfusion) as a method of organ preservation," Cryobiology, 64(3):125-143 (2012).

Scott et al., "Pancreas Oxygen Persufflation Increases ATP Levels as Shown by Nuclear Magnetic Resonance," Transplantation Proceedings, 42(6): 2011-2015 (Jul.-Aug. 2010).

Fischer, "Methods of Cardiac Oxygen Persufflation," Methods in Bioengineering: Organ Preservation and Reengineering, editors Korkut Uygun and Charles Y. Lee, published by Artech House, Norwood, MA (2011).

Treckmann et al., "Retrograde Oxygen Persufflation Preservation of Human Livers: A Pilot Study," Liver Transplantation, 14:358-64 (2008).

Koetting et al., "Optimal Time for Hypothermic Reconditioning of Liver Grafts by Venous Systemic Oxygen Persufflation in a Large Animal Model," Transplantation, 91(1):42-7 (2011).

Guibert et al., "Organ Preservation: Current Concepts and New Strategies for the Next Decade," Transfusion Medicine and Hemotherapy, 38:125-142 (2011).

Caballero-Corbalan et al., "No Beneficial Effect of Two-Layer Storage Compared with UW-Storage on Human Islet Isolation and Transplantation," 84(7):864-9 (2007).

Minor et al., "Energetic recovery in porcine grafts by minimally invasive liver oxygenation," Journal of Surgical Research, published online Mar. 14, 2012.

Taylor et al., "Current state of hypothermic machine perfusion preservation of organs: The clinical perspective," Cryobiology (2009), doi:10.1016/j.cryobiol.2009.10.006.

Scott et al., "Persufflation Improves Pancreas Preservation When Compared With the Two-Layer Method," Transplantation Proceedings, 42(6): 2016-2019 (Jul.-Aug. 2010).

J.H. Fischer: Methods of Cardiac Oxygen Persufflation. Author manuscript available at ResearchGate.net Mar. 15, 2018. Published in final edited form as: Methods of Bioengineering: Organ preservation and reengineering. Eds. Korkut Uygun and Charles Y. Lee. Artech House Boston, London 2011, p. 105-126. ISBN: 13: 978-1-60807-013-8.

Avgoustiniatos et al., "Effect of External Oxygen Mass Transfer Resistances on Viability of Immunoisolated Tissue," Ann NY Acad Sci, 831:145-167 (1997).

Barkai et al., "Enhanced Oxygen Supply Improves Islet Viability in a New Bioartificial Pancreas," Cell Transplantation, 22:1463-1476 (2013).

Bellin et al., "Potent induction immunotherapy promotes long-term insulin independence after islet transplantation in type 1 diabetes," Am J Transplant., 12(6):1576-1583 (2012).

Bergenstal et al., "Effectiveness of Sensor-Augmented Insulin-Pump Therapy in Type 1 Diabetes," N Eng J Med, 363 (4):311-320 (2010).

Goh et al., "Dual Perfluorocarbon Method to Noninvasively Monitor Dissolved Oxygen Concentration in Tissue Engineered Constructs in vitro and in vivo," Biotechnol. Prog., 27:1115-1125 (2011).

Goh et al., "In Vivo Noninvasive Monitoring of Dissolved Oxygen Concentration Within an Implanted Tissue-Engineered Pancreatic Construct," Tissue Engineering: Part C, 17(9):887-894 (2011).

Klonoff et al., "Innovations in Technology for the Treatment of Diabetes: Clinical Development of the Artificial Pancreas (an Autonomous System)," Journal of Diabetes Science and Technology, 5(3):804-826 (2011).

Ludwig et al., "A Novel Device for Islet Transplantation Providing Immune Protection and Oxygen Supply," Horm Metab Res, 42:918-922 (2010).

Luo et al., Recovery of Neurological Functions in Non-Human Primate Model of Parkinson's Disease by Transplantation of Encapsulated Neonatal Porcine Choroid Plexus Cells, Journal of Parkinson's Disease, 3: 275-291 (2013).

O'Sullivan et al., "Islets Transplanted in Immunoisolation Devices: A Review of the Progress and the Challenges that Remain," Endocrine Reviews, 32(6):827-844 (2011).

Ritz-Laser et al., "Molecular Detection of Circulating Beta-Cells After Islet Transplantation," Diabetes, 51:557-561 (2002).

Storrs et al., "Preclinical Development of the Islet Sheet," Ann NY Acad Sci, 944:252-266 (2001).

Wang et al., "Donor Treatment With Carbon Monoxide Can Yield Islet Allograft Survival and Tolerance," Diabetes, 54:1400-1406 (2005).

\* cited by examiner

PERCUTANEOUS GAS DIFFUSION DEVICE SUITABLE FOR USE WITH A SUBCUTANEOUS IMPLANT

CROSS-REFERENCE TO RELATED APPLICATIONS

The present application claims the benefit under 35 U.S.C. 119(e) of U.S. Provisional Patent Application No. 62/422,397, inventors Anthony A. Ferrante et al., filed Nov. 15, 2016, the disclosure of which is incorporated herein by reference.

BACKGROUND OF THE INVENTION

The present invention relates generally to subcutaneous implants of the type that may be used, for example, to deliver drugs, therapeutic gas, or cell-based therapeutics to a patient and relates more particularly to subcutaneous implants of the aforementioned type that require the delivery of one or more gases thereto from outside the patient and/or that require the removal of one or more gases from such implants to outside the patient.

Subcutaneous implants are useful implements for the treatment of various diseases, disorders and/or conditions. In some cases, such an implant may comprise cells and/or tissues that are encapsulated within a suitable implantable container or capsule. Alternatively or additionally, such implants may comprise a device for generating oxygen or another gas for delivery to implanted cells and/or tissues. Where cells and/or tissues are encapsulated within an implanted container, the container is typically designed to allow the cells and/or tissues to produce a desired therapeutic and for the dissemination of the produced therapeutic to the patient while, at the same time, limiting an immunological response. As can be appreciated, in some cases, access to outside air may be needed for delivery of oxygen to the implanted cells or tissues or for release of waste gases produced as a consequence of the device or cellular function.

An example that illustrates the need for cell or tissue implantation is the development of cellular therapies for the treatment of diabetes. Currently, cell-based treatment options for diabetes treatment include whole pancreas organ transplant or transplant of pancreatic islets of Langerhans. However, because of the need for lifelong immunosuppressive treatment, these therapies are typically reserved for patients with the most difficult to treat Type 1 diabetes, particularly those who are already receiving immunosuppressive therapy as a result of a previous or concurrent organ transplant.

Containers or capsules have been developed that enable implantation of islets and other tissues without the need for immunosuppression. For example, some currently available cell capsules incorporate an immunoisolating membrane that protects allogenic encapsulated tissue from the host immune system; however, unfortunately, such an immunoisolating membrane also prevents vascularization of the encapsulated tissue, thereby making the delivery of essential gases to the encapsulated tissue and the removal of waste gases therefrom more difficult. While safety and cell protection for capsules has been well-documented, such approaches have ultimately failed to realize the anticipated benefits due to limitations in oxygen delivery to the encapsulated cells. (See the following, all of which are incorporated herein by reference in their entireties: Suzuki et al., "Number and volume of islets transplanted in immunobarrier devices," *Cell transplantation*, 7:47-52 (1998); Tibell et al., "Survival of macroencapsulated allogeneic parathyroid tissue one year after transplantation in nonimmunosuppressed humans," *Cell transplantation*, 10:591-9 (2001); Bruin et al., "Maturation and function of human embryonic stem cell-derived pancreatic progenitors in macroencapsulation devices following transplant into mice," *Diabetologia*, 56:1987-98 (2013); Motté et al., "Composition and Function of Macro-Encapsulated Human Embryonic Stem Cell-Derived Implants: Comparison with Clinical Human Islet Cell Grafts," *Am J Physiol Endocrinol Metab.*, 307: E838-46 (2014); Yanay et al., "Long-term erythropoietin gene expression from transduced cells in bioisolator devices," *Human gene therapy*, 14:1587-93 (2003); Bartholomew et al., "Baboon mesenchymal stem cells can be genetically modified to secrete human erythropoietin in vivo," *Human gene therapy*, 12:1527-41 (2001); Sweet et al., "Treatment of diabetic rats with encapsulated islets," *J. Cell. and Mol. Med.*, 12: 2644-50 (2008); Sorenby et al., "Macroencapsulation protects against sensitization after allogeneic islet transplantation in rats," *Transplantation*, 82:393-7 (2006); Colton, "Implantable biohybrid artificial organs," *Cell transplant.*, 4:415-36 (1995); Moralejo et al., "Sustained glucagon-like peptide 1 expression from encapsulated transduced cells to treat obese diabetic rats," *J. Biosci. and Bioeng.*, 111:383-7 (2011); Chou et al., "Treatment of osteoporosis with TheraCyte-encapsulated parathyroid cells: a study in a rat model," *Osteoporosis International: a journal established as result of cooperation between the European Foundation for Osteoporosis and the National Osteoporosis Foundation of the USA*, 17:936-41 (2006).)

In an attempt to address the above-noted limitations in oxygen delivery to implanted cells, several methods to deliver oxygen to cell capsules are under development. These include periodic injection of compressed, gaseous oxygen through the skin to an implanted device (see Ludwig et al., "Improvement of islet function in a bioartificial pancreas by enhanced oxygen supply and growth hormone releasing hormone agonist," *Proc. Nat. Acad. Sci. U.S.A.*, 109:5022-7 (2012), which is incorporated herein by reference in its entirety), delivery of oxygen to cell capsules through a percutaneous catheter, implantation of chemical oxygen generators (see McQuilling et al., "Methods for Incorporating Oxygen-Generating Biomaterials into Cell Culture and Microcapsule Systems," *Methods Mol. Biol.*, 1479:135-141 (2017), and Pedrazaa et al., "Preventing hypoxia-induced cell death in beta cells and islets via hydrolytically activated, oxygen-generating biomaterials," *Proc. Natl. Acac. Sci. U.S.A.*, 109:4245-4250 (2012), both of which are incorporated herein by reference in their entireties), and implantation of electrochemical oxygen generating devices (see, for example, U.S. Pat. No. 6,368,592 B1, inventors Colton et al., issued Apr. 9, 2002, and U.S. Patent Application Publication No. US 2015/0112247 A1, inventors Tempelman et al., published Apr. 23, 2015, both of which are incorporated herein by reference in their entireties).

Unfortunately, however, many of the above approaches have limitations. For example, the injection of pressurized oxygen requires that the user pierce the skin on a regular basis and requires periodic replacement of the septum in the device. The failure to properly penetrate the septum with the needle could introduce gaseous oxygen to unwanted areas of the body, which may be hazardous. The delivery of oxygen through a percutaneous line carries a risk of infection, and associated devices are undesirably exposed to the environment. Chemical oxygen generators can be fully implantable and may be useful as a temporary source of oxygen, but there are some concerns about the materials used and side effects, such as local pH changes. In addition, the substrate for the oxygen generation reaction is consumed over time and will eventually result in cessation of oxygen delivery, requiring subsequent surgical or percutaneous product drainage and substrate refilling.

Implantable electrochemical oxygen generators (EOGs, also referred to herein and in the art as water electrolyzers) address many of the limitations of the other approaches described above. Implantable electrochemical oxygen generators typically electrolyze water that is harvested from the body to generate oxygen gas at the anode and to generate hydrogen gas at the cathode. The generated oxygen is then delivered to cells, and the generated hydrogen may then diffuse through the tissue to the vasculature and eventually be exhaled. Due to reaction stoichiometry, hydrogen is typically generated at twice the rate as oxygen. The safe diffusion of hydrogen from the cathode to the body requires significant surface area to prevent gas bubble formation at the device/tissue interface. However, unfortunately, the requirement for adequate gas-tissue interface surface area increases the size and complexity of an implanted device.

Implantable electrochemical oxygen concentrators (EOCs) provide an alternative to implantable EOGs for delivery of oxygen to implanted cells. EOCs function similarly to electrolyzers, but they consume oxygen from air to produce water at the cathode and generate oxygen from water at the anode, with the net effect being that oxygen is concentrated at the anode for delivery to a downstream device. The fundamental reactions that occur are:

$$2H_2O \rightarrow 4H^+ + 4e^- + O_2(\text{pure}) \quad (1) \text{ Anode (Oxidation: loss of electrons):}$$

$$O_2 + 4H^+ + 4e^- \rightarrow 2H_2O \quad (2) \text{ Cathode (Reduction: gain of electrons):}$$

$$\text{dilute } O_2 \text{ at cathode} \rightarrow \text{pure } O_2 \text{ at anode} \quad (3) \text{ Net:}$$

In both EOGs and EOCs, oxygen generation (i.e., nutrient dose to cells) corresponds precisely to the current that is applied. Because EOCs typically operate at about 0.8V, and EOGs typically operate at about 1.6V, EOCs typically use approximately half as much power as EOGs. On the other hand, EOCs typically require access to extracorporeally-derived oxygen (i.e., air) to replenish the oxygen consumed at the cathode. Moreover, regardless of whether an EOG or an EOC is used, it may be desirable to provide a pathway by which waste gases produced as a consequence of the device or cellular function may be expelled from the body.

SUMMARY OF THE INVENTION

The present inventors have identified a need to provide a pathway for diffusion of one or more gases (e.g., air, oxygen gas, hydrogen gas) between the ambient environment outside the body and a device implanted in a patient, such as, but not limited to, an implanted EOC, an implanted EOG, or an implanted container holding implanted cells and/or tissue, thus enabling the use of the implanted device while limiting opportunities for infection.

It is an object of the invention to provide such a pathway.

Therefore, according to one aspect of the invention, there is provided a percutaneous gas diffusion device, the percutaneous gas diffusion device comprising (a) a core layer, the core layer having a length, a bottom, and a periphery, the core layer being gas-permeable and liquid-impermeable; and (b) an outer layer, the outer layer surrounding the periphery of the core layer for at least a portion of the length of the core layer, the outer layer comprising a tissue-integrating material.

In a more detailed feature of the invention, the core layer may have an open-pore structure.

In a more detailed feature of the invention, the core layer may have a pore diameter up to 0.22 μm.

In a more detailed feature of the invention, the core layer may have a closed-pore structure.

In a more detailed feature of the invention, the core layer may be a nonporous solid material.

In a more detailed feature of the invention, the core layer may comprise at least one material selected from the group consisting of porous polymers, non-porous gas-permeable materials, an open-cell ceramic foam, and a porous metal.

In a more detailed feature of the invention, at least one material of the core layer may be treated with a hydrophobic polymer.

In a more detailed feature of the invention, the core layer may be cylindrical in shape.

In a more detailed feature of the invention, the core layer may have a diameter of no more than 5 mm and a length of 1.2-10 mm.

In a more detailed feature of the invention, the core layer may have a diameter of no more than 1 mm and a length of 2-5 mm.

In a more detailed feature of the invention, the tissue-integrating material of the outer layer may be at least one porous, biocompatible material selected from the group consisting of open-cell silicone foams, patterned microporous materials, open-cell urethane foams, sintered polymeric materials.

In a more detailed feature of the invention, the outer layer may have a thickness of 0.2-1.0 mm and a length of 1.2-2.0 mm.

In a more detailed feature of the invention, the outer layer may have a length, and the length of the outer layer may match the length of the core layer.

In a more detailed feature of the invention, the outer layer may have a bottom, and the bottom of the core may extend downwardly beyond the bottom of the outer layer.

In a more detailed feature of the invention, the core layer may be fixedly coupled to the outer layer.

In a more detailed feature of the invention, the core layer may be removably coupled to the outer layer.

In a more detailed feature of the invention, a portion of the core layer may be fixedly coupled to the outer layer, and a portion of the core layer may be removably coupled to the outer layer.

In a more detailed feature of the invention, the percutaneous gas diffusion device may further comprise an intermediate layer, and the intermediate layer may be positioned between the core layer and the outer layer.

In a more detailed feature of the invention, the intermediate layer may comprise a barrier that prevents infiltration of tissue from the outer layer into the core layer.

In a more detailed feature of the invention, the intermediate layer may comprise a barrier that prevents infiltration of tissue from the outer layer into the core layer and that reduces diffusion of gas from the core layer into the outer layer.

In a more detailed feature of the invention, the intermediate layer may have a bottom, the outer layer may have a bottom, and the bottom of the intermediate layer may extend downwardly beyond the bottom of the outer layer.

In a more detailed feature of the invention, at least one of the core layer and the intermediate layer may be configured to permit the removable coupling of at least a portion of the core layer to the intermediate layer.

In a more detailed feature of the invention, the core layer may comprise at least one notch adapted for engagement with a tool.

In a more detailed feature of the invention, the intermediate layer may comprise at least one notch adapted for engagement with a tool.

In a more detailed feature of the invention, the core layer and the intermediate layer may have mating threads.

In a more detailed feature of the invention, the intermediate layer may comprise a bottom portion shaped for coupling to an implant device.

In a more detailed feature of the invention, the bottom portion of the intermediate layer may comprise at least one rib.

In a more detailed feature of the invention, the bottom portion of the intermediate layer may comprise a circumferential groove.

It is another object of the present invention to provide an implant system.

Therefore, according to one aspect of the invention, there is provided an implant system, the implant system comprising (a) an implant device, the implant device comprising at least one of a gas inlet and a gas outlet; (b) a percutaneous gas diffusion device, the percutaneous gas diffusion device being fluidically coupled to one of the gas inlet and the gas outlet of the implant device, the percutaneous gas diffusion device comprising (i) a core layer, the core layer being gas-permeable and liquid-impermeable; and (ii) an outer layer, the outer layer surrounding a periphery of the core layer for at least a portion of a length of the core layer, the outer layer comprising a tissue-integrating material.

In a more detailed feature of the invention, the implant device may be a subcutaneous container for holding at least one of implanted cells and implanted tissue, the subcutaneous container may comprise an oxygen inlet, and the percutaneous gas diffusion device may be fluidically coupled to the oxygen inlet.

In a more detailed feature of the invention, the implant device may be a subcutaneous electrochemical oxygen concentrator, the subcutaneous electrochemical oxygen concentrator may comprise an air inlet, and the percutaneous gas diffusion device may be fluidically coupled to the air inlet.

In a more detailed feature of the invention, the implant device may be a subcutaneous water electrolyzer, and the subcutaneous water electrolyzer may comprise an oxygen outlet and a hydrogen outlet.

In a more detailed feature of the invention, the percutaneous gas diffusion device may be fluidically coupled to the oxygen outlet.

In a more detailed feature of the invention, the percutaneous gas diffusion device may be fluidically coupled to the hydrogen outlet.

In a more detailed feature of the invention, the implant device may be a subcutaneous electrochemical cell capable of alternatively operating in an electrochemical oxygen concentrator mode and an electrochemical oxygen generator mode.

The present invention is also directed at a method of using an implant device.

Therefore, according to one aspect of the invention, there is disclosed a method of using an implant device, the method comprising the steps of (a) providing an implant system as described above, wherein the implant system is a subcutaneous electrochemical cell capable of alternatively operating in an electrochemical oxygen concentrator mode and an electrochemical oxygen generator mode; (b) implanting the implant system in a patient; (c) then, operating the implant system in the electrochemical oxygen concentrator mode, whereby contaminants contaminate the core layer of the percutaneous gas diffusion device; and (d) then, operating the implant system in the electrochemical oxygen generator mode to expel the contaminants from the core layer of the percutaneous gas diffusion device.

For purposes of the present specification and claims, various relational terms like "top," "bottom," "proximal," "distal," "upper," "lower," "front," and "rear" may be used to describe the present invention when said invention is positioned in or viewed from a given orientation. It is to be understood that, by altering the orientation of the invention, certain relational terms may need to be adjusted accordingly.

Additional objects, as well as aspects, features and advantages, of the present invention will be set forth in part in the description which follows, and in part will be obvious from the description or may be learned by practice of the invention. In the description, reference is made to the accompanying drawings which form a part thereof and in which is shown by way of illustration various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. These drawings are not necessarily drawn to scale, and certain components may have undersized and/or oversized dimensions for purposes of explication. In the drawings wherein like reference numeral represent like parts.

DETAILED DESCRIPTION OF THE INVENTION

Figure 1A:
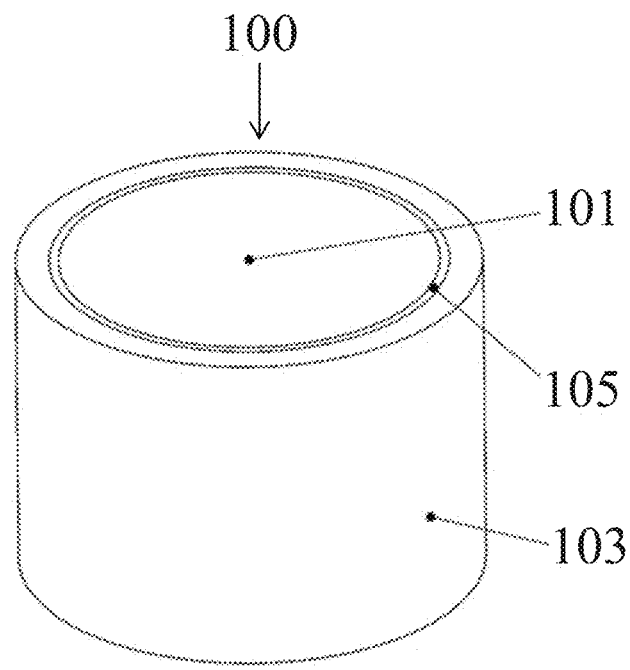
FIGS. 1A through 1C are perspective, top, and section views, respectively, of a first embodiment of a percutaneous gas diffusion device constructed according to the present invention for permitting the passage of one or more gases to and/or from an implant in a patient.
Figure 1B:
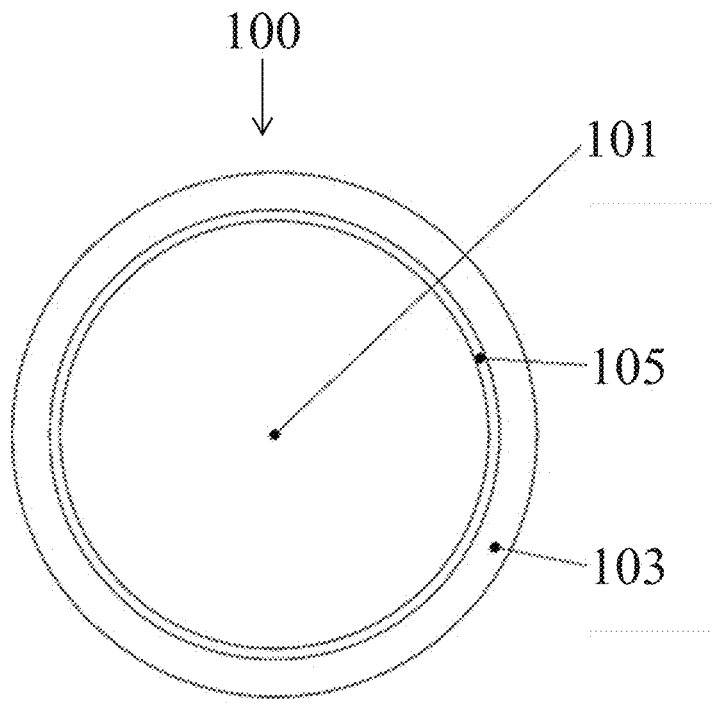
Figure 1C:
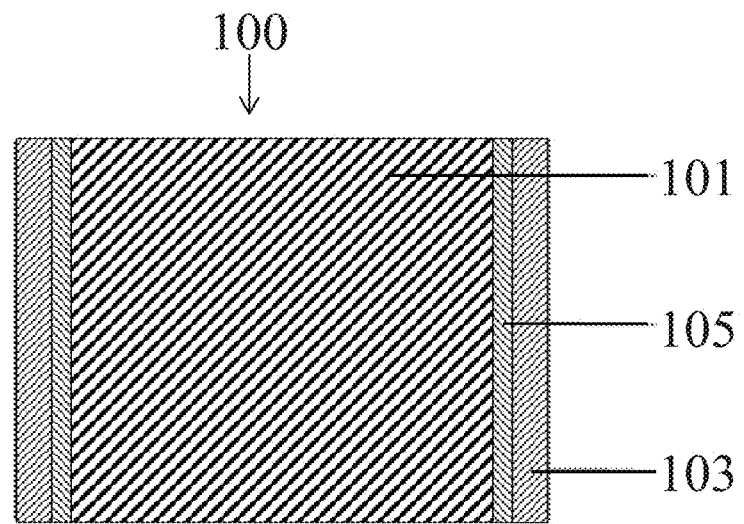
Figure 1D:
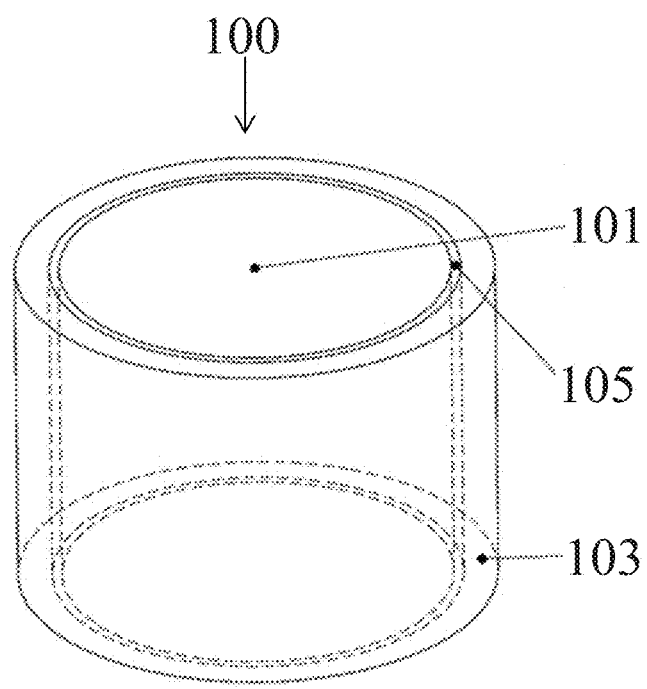
FIG. 1D is a perspective view of the percutaneous gas diffusion device of FIG. 1A, with phantom lines being used to delineate the constituent layers of the percutaneous gas diffusion device.

The present invention is directed, at least in part, to a percutaneous gas diffusion device that allows ambient air or other extracorporeal gases to flow to an implanted device positioned within a patient and/or that allows gases to flow from the implanted device to a location outside the body of the patient. The implanted device may be a subcutaneous implant, such as, but not limited to, an electrochemical oxygen generator, an electrochemical oxygen concentrator, or a container holding one or more implanted cells and/or tissues.

More specifically, in certain embodiments, the present invention may be a percutaneous device that allows oxygen, water vapor, and other gases to pass through the skin, but that prevents passage of liquids and particulates. The invention thus enables the use of implanted medical devices that require access to air outside the body either for access to key gases, such as oxygen or water vapor, or for efficient elimination of waste gases, such as hydrogen or oxygen in the case of an implanted water electrolyzer.

In certain embodiments, the passage of gases through the percutaneous device can be passive, and, in certain embodiments, the passage of gases through the percutaneous device can be actively promoted by a device component that is either implanted or worn externally.

In certain embodiments, the percutaneous device may comprise one or more concentric layers. The outer layer (or peripheral layer) may incorporate materials known to integrate with tissue and, thus, may form a barrier that minimizes the risk of infection. Suitable materials for the outer layer may be microporous and biocompatible including, but not limited to, open-cell silicone foams, patterned microporous materials, and open-cell urethane foams. An example of a suitable patterned microporous material may be STAR® (Sphere Templated Angiogenic Regeneration) biomaterial scaffold (Healionics Corporation, Seattle, Wash.), which is described in U.S. Pat. No. 8,647,393 B2, inventors Marshall et al., issued Feb. 11, 2014, Marshall et al., "Dermal Integration Cuff Improves Resistance to Exit Site Infections in Porcine Bacterial Challenge," Abstract 072, Society for Biomaterials (2011), and Fukano et al., *J Biomed Mater Res A*, 94(4): 1172-1186 (2010), all of which are incorporated herein by reference. Additional materials that may be suitable for the outer layer may include hard materials, such as, but not limited to, biocompatible ceramic foams and sintered biocompatible polymers (e.g., sintered polytetrafluoroethylene (PTFE), sintered polyvinylidene fluoride (PVDF), sintered polyethylene, and sintered polypropylene).

The inner layer (or core layer or core) may comprise a gas-permeable layer or gas-permeable composite of layers, through which one or more gases including, but not limited to, oxygen, nitrogen, nitric oxide, hydrogen, hydrogen sulfide, carbon dioxide, and water vapor may diffuse. Materials that may be used to form the inner layer may include, but are not limited to, porous polymers (e.g., open cell silicone foam, open cell urethane foam, sintered polyethylene, sintered polypropylene, sintered PVDF, sintered PTFE), microporous materials, such as ceramic foam or porous titanium, and non-porous, gas-permeable materials (e.g., silicone membranes). Microporous materials may be further treated to change their surface properties. For example, a naturally hydrophilic porous ceramic or metal may be coated with a polymer, such as a Parylene™ poly(p-xylylene) polymer, so that the coated material is hydrophobic. Use of hydrophobic, microporous structures, or materials that are permeable to gases and vapor phase water at the core of the device may be desirable as it allows gas exchange while preventing migration of liquid water, which may carry contaminants, including infectious agents, across the skin.

The inner (or core) layer and the outer (or peripheral) layer, which may be fixedly coupled to one another, may be in direct contact with one another or may be separated by one or more intermediate layers. Such intermediate layers may function to prevent the ingrowth of tissue from the peripheral layer into the core layer. The one or more intermediate layers may also have lower gas permeability than the core layer and, thus, may minimize gas exchange between the core layer and the surrounding tissue. For example, an intermediate layer that is impermeable to oxygen would prevent tissue in the peripheral layer from lowering oxygen concentrations in the core layer and would result in higher oxygen concentrations where the core layer connects to an implanted medical device, such as an EOC. Examples of materials that may be suitable for use as the one or more intermediate layers may include, but are not limited to, silicone membranes; microporous membranes formed from PTFE, PVDF, polyethersulfone, and polyethylene terephthalate; flexible non-porous materials, such as PTFE, polyethylene, and polypropylene; and rigid, non-porous materials including polyether ether ketone (PEEK), other biocompatible polymers, ceramics, and metals, such as implant grade stainless steel and titanium.

In certain embodiments, properties of the peripheral layer and/or the core layer may perform the function of a tissue barrier layer. For example, during fabrication of a porous silicone tissue integration (or outer) layer, a "skin" may form that may act as a cell barrier, independent of a separate element. In certain embodiments, the manner of attaching the tissue integration layer to the gas-permeable core may form a de facto tissue barrier layer. For example, a silicone adhesive that forms a tissue barrier may be used to attach a tissue integration layer to a gas-permeable core. In certain embodiments, the gas-permeable core may have a sufficiently small pore size that it may act independently as a tissue barrier layer to prevent tissue ingrowth.

In certain embodiments, the percutaneous gas diffusion device may be directly or indirectly connected to a cell capsule or cell container. In certain embodiments, the percutaneous gas diffusion device may be connected to an electrochemical device that consumes oxygen at the cathode and that produces oxygen at the anode for delivery to implanted cells, effectively acting as an oxygen concentrator. In certain embodiments, the percutaneous gas diffusion device may be connected to an electrochemical device that consumes water delivered in the form of water vapor to produce hydrogen gas at the cathode and oxygen gas at the anode for delivery to implanted cells. In certain embodiments, the percutaneous gas diffusion device may be connected to an electrochemical device that consumes water delivered in the form of water vapor to produce oxygen gas at the anode and hydrogen at the cathode for delivery to implanted cells or systemically to the body via the circulatory system. In certain embodiments, waste gases generated by an electrochemical device may be eliminated through the percutaneous gas diffusion device and exhausted to the air. In certain embodiments, gases that are consumed by an electrochemical device may be replenished by diffusion through the percutaneous gas diffusion device.

In embodiments where the gas-permeable core is porous, pores within the gas-permeable core preferably remain open for free diffusion of gases. In the example of a water electrolyzer coupled to the percutaneous gas diffusion device of the present invention, either oxygen or hydrogen may flow out through the gas-permeable core and may expel water or other liquid that may have infiltrated the material. In the case of an EOC, there is no net production of gas to force liquids or other materials from the gas permeable core. In certain embodiments, an electrochemical device may perform as an EOC when the gas-permeable core is unblocked but may revert to electrolyzer mode when oxygen concentrations fall below that required to react to form water vapor at the cathode. In this case, operation in electrolyzer mode may clear the gas-permeable core and may ultimately enable the electrochemical device to switch back to the more efficient EOC mode. In certain embodiments, the electrochemical device might cycle between EOC and EOG modes in which the hydrogen gas formed during the EOG mode acts to expel contaminants from the gas-permeable core material.

Referring now to FIGS. 1A through 1D, there are shown various views of a first embodiment of a percutaneous gas diffusion device suitable for permitting the passage of one or more gases to and/or from an implant in a patient, the percutaneous gas diffusion device being constructed according to the present invention and represented generally by reference numeral 100.

Percutaneous gas diffusion device 100 may comprise a core layer 101, an outer layer 103, and an intermediate layer 105. In the present embodiment, core layer 101, outer layer 103, and intermediate layer 105 may be fixed relative to one another.

Core layer 101 may comprise a material or composite of materials that are liquid-impermeable and gas-permeable. In this manner, for example, ambient air or external gases may diffuse through core layer 101 to an inlet port of a subcutaneously-implanted EOC or EOG device and/or by-product gases from the subcutaneous EOC or EOG device or waste gases from implanted cells and/or tissues may diffuse through core layer 101 to exit a body. Core layer 101 may comprise an open-pore structure, a closed-pore structure, or may be a solid material. The gas diffusion properties of core layer 101 may be non-selective, as in the case of an open-pore structure, or may be selective, as in the case of a closed-pore structure or solid matrix. By using a closed-pore structure, or an open-pore structure with small pores and high hydrophobicity, the inner core material may be substantially impermeable to external liquid contaminants. Examples of materials that may be used as core layer 101 or as a component of core layer 101 may include, but are not limited to, porous polymers (e.g., silicone foam, urethane foam, sintered polyethylene, sintered polypropylene, sintered PVDF, sintered PTFE), non-porous, gas-permeable materials (e.g., silicone membranes), and combinations thereof. Core layer 101 may also comprise an open-cell ceramic foam or a porous metal, such as sintered titanium. The porous material may be further treated to alter its hydrophobicity. For example, the porous material may be coated with a polymer, such as a Parylene™ poly(p-xylylene) polymer. Such Parylene™ poly(p-xylylene) polymers may include Parylene-N, Parylene-C, Parylene-D, and, preferably, Parylene-VT4 and Parylene AF4. If an open pore material is used, the porosity diameter may be appropriate to provide a barrier to microorganisms. In certain embodiments, the porosity diameter may be equal to or less than 0.22 µm, and, in certain embodiments, the porosity diameter may be equal to or less than 0.2 µm.

In the present embodiment, core layer 101 is shown as being cylindrical in shape; however, it is to be understood that core layer 101 is not limited to a cylindrical shape and can assume a variety of alternative shapes. The diameter of core layer 101 may be varied, depending on the gas-exchange requirements of percutaneous gas diffusion device 100; nevertheless, according to some embodiments, the diameter of core layer 101 may be less than or equal to 5 mm, preferably less than or equal to 1 mm. The length of core layer 101 is preferably sufficient to provide a gas diffusion path from an implanted medical device through the skin to the atmosphere. For example, such a length may be approximately 1.2-10 mm, preferably approximately 2-5 mm.

Outer layer 103, which may extend the entire length of core layer 101, may comprise a tissue-integration material, namely, a porous, biocompatible material that promotes the growth of skin tissue into said material. The tissue-integration material may comprise an open-pore structure with connections between pores through which cells can migrate. The tissue-integration material may be formed using a micro-patterned template for tight control over pore size. Such materials may be readily processed to form hollow cylinders. The tissue-integration materials may be further optimized to promote tissue integration, thus preventing infection. Preferred tissue-integration materials may be flexible and may move with the skin during normal activity, thus reducing chronic inflammation at the tissue interface. Examples of tissue-integration materials may include, but are not limited to, open-cell silicone foams, patterned microporous materials, open-cell urethane foams, sintered polymeric materials (e.g., PTFE, PVDF, polyethylene and polypropylene), and combinations thereof. Examples of suitable patterned microporous materials may include STAR® (Sphere Templated Angiogenic Regeneration) biomaterial scaffold (Healionics Corporation, Seattle, Wash.) or other similar materials fabricated from silicone or polyhydroxyethylmethacrylate.

Outer layer 103 may have a wall thickness of about 100 nm to several millimeters but preferably is approximately 0.2-1.0 mm. The length of outer layer 103 is preferably sufficient to span the dermis and may range from about 1.2-2.0 mm. Although outer layer 103 is shown in the present embodiment as having a length that spans the entire length of core layer 101, it is to be understood that outer layer 103 may be shorter than core layer 101. In fact, outer layer 103 may not extend to the interface of the percutaneous gas diffuser and an implanted device surface.

Intermediate layer 105, which is positioned between core layer 101 and outer layer 103, may function as a barrier layer between core layer 101 and outer layer 103. More specifically, intermediate layer 105 may prevent infiltration of tissue into core layer 101 from outer layer 103 and may prevent contaminants in core layer 101 from coming into contact with outer layer 103. Intermediate layer 105 may comprise a single layer of material or multiple layers of material. Suitable materials for use in forming intermediate layer 105 may include, but are not limited to, nanoporous and non-porous polymer membranes, nanoporous and non-porous metals, and nanoporous and non-porous ceramics. The wall thickness of intermediate layer 105 may vary, depending on the material used and/or on the need to interact with the implanted device; nevertheless, in certain embodiments, intermediate layer 105 may range from about 10 nm to 1 mm. In the present embodiment, intermediate layer 105 extends the entire length of core layer 101. However, it is to be understood that intermediate layer 105 need not extend the entire length of core layer 101; nevertheless, intermediate layer 105 preferably extends a sufficient length to protect core layer 101 from tissue integration.

Intermediate layer 105 may comprise a material that may or may not enable diffusion of gases between core layer 101 and outer layer 103. Having intermediate layer 105 act as a barrier to prevent cell migration into core layer 101 and additionally prevent gas diffusion is especially desirable if core layer 101 is an open-cell foam material. Examples of materials that may be used as intermediate layer 105 and that may prevent cell migration and also limit gas diffusion between core layer 101 and outer layer 103 may include, but are not limited to, biocompatible fluoropolymers (e.g., PTFE and PVDF), other biocompatible polymers (e.g., polypropylene and polyethylene), and rigid biocompatible metals (e.g., implantable stainless steel and titanium). Examples of materials that may be used as intermediate layer 105 layer and that may prevent cell migration and are gas-permeable include, but are not limited to, microporous polymer membranes and tubing (e.g., expanded-PTFE, PVDF, open-cell silicone foam, and open-cell urethane foam), and gas-permeable solid membranes and tubing (e.g., silicone and urethane).

In certain embodiments, properties of core layer 101 and/or outer layer 103 may perform at least some of the functions of intermediate layer 105. For example, during fabrication of a porous silicone outer layer 103, a "skin" may form along the outside that may act as a cell barrier, independent of a separate element. In certain embodiments, the manner of attaching outer layer 103 to core layer 101 may form a de facto barrier layer. For example, a silicone adhesive that may form a tissue barrier may be used to attach outer layer 103 to core layer 101. In certain embodiments, the gas-permeable core layer 101 may have a sufficiently small pore size that it acts independently of a barrier layer to prevent tissue ingrowth.

Figure 2:
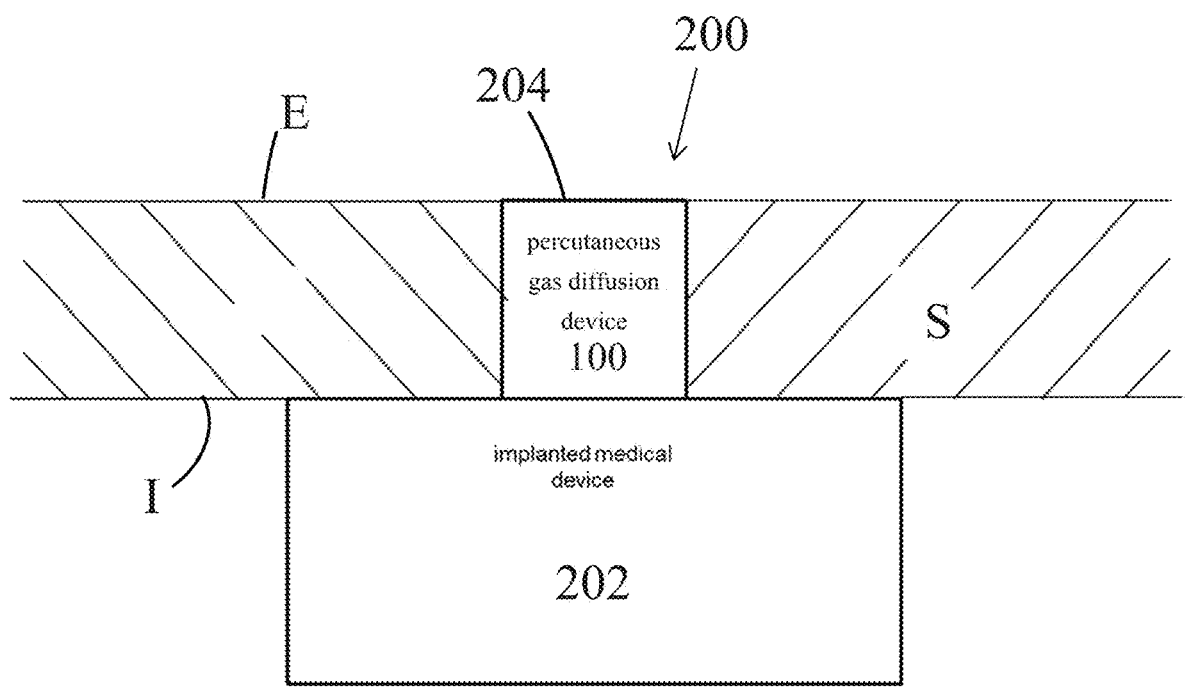
FIG. 2 is a block diagram, partly in section, showing a first embodiment of an implant system constructed according to the present invention, the implant system being shown implanted in a patient and comprising the percutaneous gas diffusion device of FIG. 1A extending through the skin of a patient and an implanted medical device positioned under the skin of the patient and coupled to the percutaneous gas diffusion device of FIG. 1A.

Referring now to FIG. 2, there is schematically shown a first embodiment of an implant system constructed according to the present invention, the implant system being shown implanted in a patient and being represented generally by reference numeral 200. (For simplicity and clarity, certain components of implant system 200 that are not critical to an understanding of the present invention are either not shown or described herein or are shown and/or described herein in a simplified manner.)

Implant system 200 may comprise percutaneous gas diffusion device 100 and an implanted medical device 202. As can be seen, percutaneous gas diffusion device 100 may be appropriately dimensioned so that the top 204 of percutaneous gas diffusion device 100 is located near the exterior surface E of a patient's skin S, preferably at or slightly above the exterior surface E. The bottom of percutaneous gas diffusion device 100 may extend below the interior surface I of the patient's skin S and is fluidically coupled to an implanted medical device 202, which may be, for example, a subcutaneously-implanted EOC, a subcutaneously-implanted EOG, a subcutaneously-implanted container holding implanted cells and/or tissue, or any other subcutaneously-implanted or other implanted device or structure for which it may be desirable or advantageous to transfer gases through the skin without the use of a percutaneous catheter.

As discussed above, the outer layer of percutaneous gas diffusion device 100 promotes the ingrowth of tissue from the patient's skin S thereinto to form an integrated structure that includes cells, including immune cells, basement membrane proteins dermal collagen bundles, and blood vessels. The integrated structure thus forms a barrier to prevent infection. Although not shown, tissue ingrowth extends to the intermediate layer of percutaneous gas diffusion device 100, said intermediate layer being formed of a material whose composition and/or pore structure preferably prevents cell penetration.

Figure 3A:
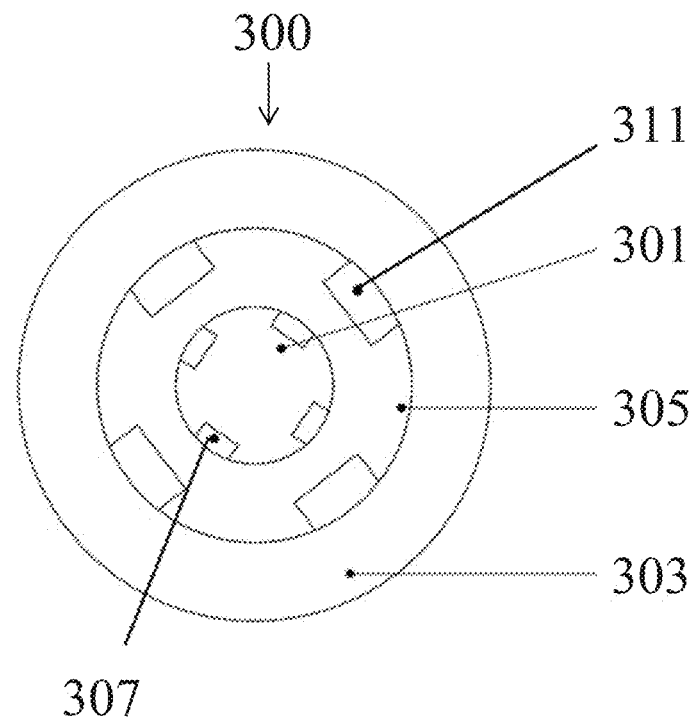
FIGS. 3A and 3B are top and section views, respectively, of a second embodiment of a percutaneous gas diffusion device constructed according to the present invention for permitting the passage of one or more gases to and/or from an implant in a patient.
Figure 3B:
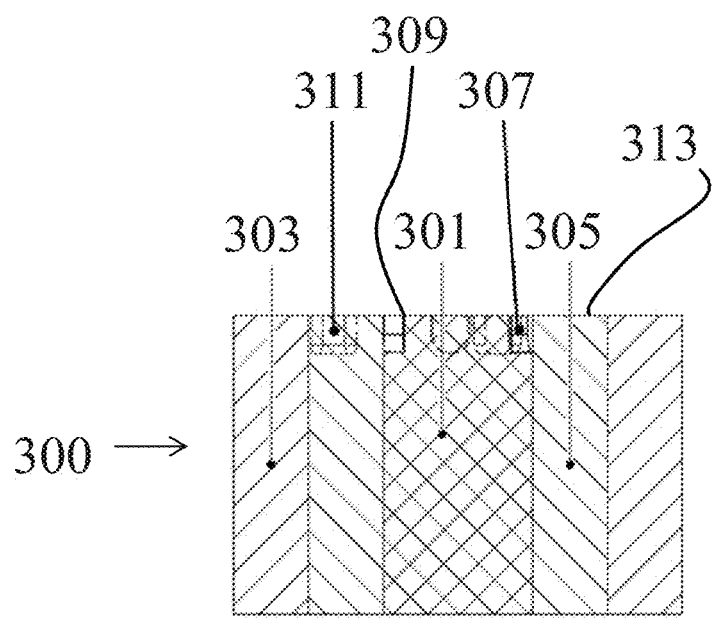

Referring now to FIGS. 3A and 3B, there are shown various views of a second embodiment of a percutaneous gas diffusion device constructed according to the present invention for permitting the passage of one or more gases to and/or from an implant in a patient, the percutaneous gas diffusion device being represented generally by reference numeral 300.

Percutaneous gas diffusion device 300 may comprise a core layer 301, an outer layer 303, and an intermediate layer 305. Percutaneous gas diffusion device 300 may be similar in most respects to percutaneous gas diffusion device 100, except that percutaneous gas diffusion device 300 may be constructed so that, when desired, core layer 301 may be removed from within intermediate layer 305, for example, to permit its replacement. In this manner, for example, core layer 301 may be changed on a regular basis as part of preventative maintenance or only as needed when it becomes soiled or clogged.

Accordingly, in the present embodiment, core layer 301 may be identical to core layer 101 of percutaneous gas diffusion device 100, except that core layer 301 may include one or more notches 307 extending downwardly a short distance from a top surface 309 of core layer 301. Notches 307 may be sized and shaped to facilitate the removal of core layer 301 from within intermediate layer 305, for example, using a complementarily-shaped tool. Intermediate layer 305 may be identical to intermediate layer 105 of percutaneous gas diffusion device 100, except that intermediate layer 305 may include one or more notches 311 extending downwardly a short distance from a top surface 313 of intermediate layer 305. Notches 311 may be sized and shaped to interact, for example, with a complementarily-shaped tool to keep intermediate layer 305 stationary while core layer 301 is being removed therefrom.

Percutaneous gas diffusion device 300 is preferably constructed so that core layer 301, outer layer 303, and intermediate layer 305 do not move relative to one another unless core layer 301 is being removed from intermediate layer 305, for example, in the manner described above. Otherwise, percutaneous gas diffusion device 300 may be used in a manner similar to that described above for percutaneous gas diffusion device 100.

Figure 4:
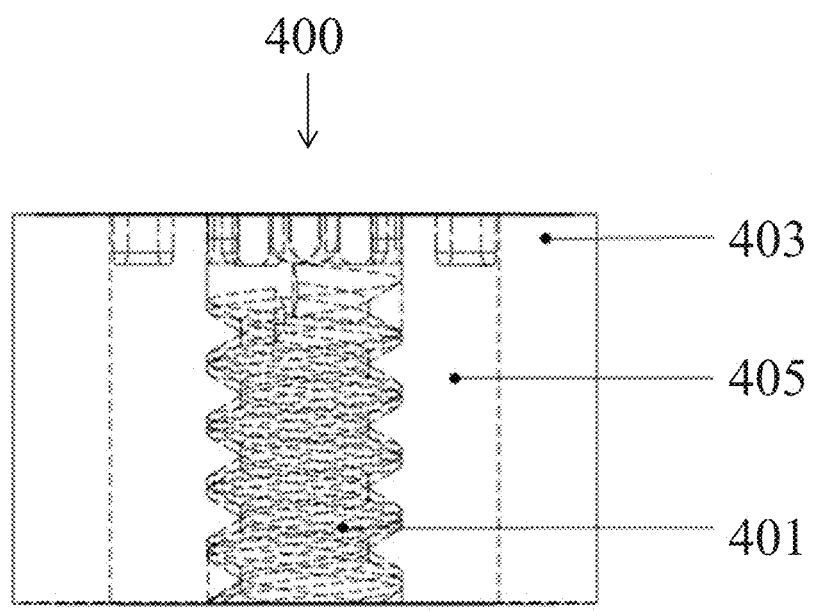
FIG. 4 is a section view of a third embodiment of a percutaneous gas diffusion device constructed according to the present invention for permitting the passage of one or more gases to and/or from an implant in a patient.

Referring now to FIG. 4, there is shown a section view of a third embodiment of a percutaneous gas diffusion device constructed according to the present invention for permitting the passage of one or more gases to and/or from an implant in a patient, the percutaneous gas diffusion device being represented generally by reference numeral 400. (For clarity, cross-hatching has been omitted from FIG. 4.)

Percutaneous gas diffusion device 400 may comprise a core layer 401, an outer layer 403, and an intermediate layer 405. Core layer 401 and intermediate layer 405 may be similar to core layer 301 and intermediate layer 305, respectively, of percutaneous gas diffusion device 300, except that core layer 401 and intermediate layer 405 may be complementarily threaded to permit core layer 401 and intermediate layer 405 to be coupled and decoupled by screwing. Outer layer 403 may be identical to outer layer 303 of percutaneous gas diffusion device 300.

Percutaneous gas diffusion device 400 may be used in manner similar to that described above for percutaneous gas diffusion device 100.

Figure 5:
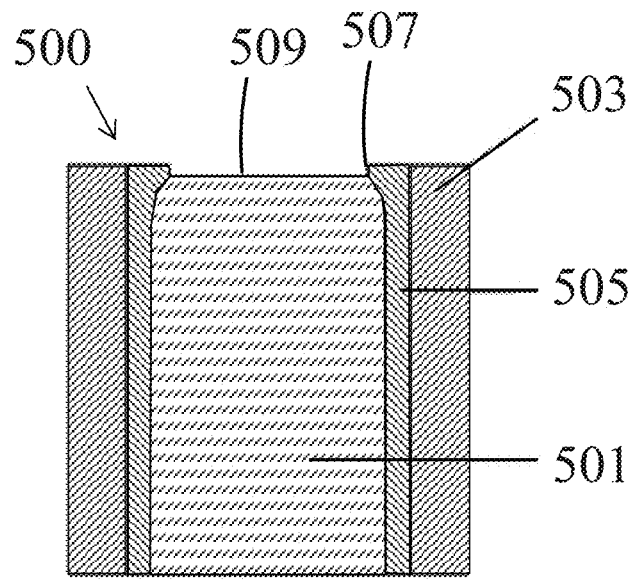
FIG. 5 is a section view of a fourth embodiment of a percutaneous gas diffusion device constructed according to the present invention for permitting the passage of one or more gases to and/or from an implant in a patient.

Referring now to FIG. 5, there is shown a section view of a fourth embodiment of a percutaneous gas diffusion device constructed according to the present invention for permitting the passage of one or more gases to and/or from an implant in a patient, the percutaneous gas diffusion device being represented generally by reference numeral 500.

Percutaneous gas diffusion device 500 may comprise a core layer 501, an outer layer 503, and an intermediate layer 505. Core layer 501, outer layer 503, and intermediate layer 505 may be similar to core layer 101, outer layer 103, and intermediate layer 105, respectively, of percutaneous gas diffusion device 100, except that core layer 501, outer layer 503, and intermediate layer 505 may be constructed so that core layer 501 may be releasably retained within intermediate layer 505. More specifically, intermediate layer 505 may include, at its top end, a flange 507 that may extend over a top surface 509 of core layer 501 to keep core layer 501 in place. Core layer 501 and/or intermediate layer 505 may be made of a pliant material that may permit core layer 501 to be moved past flange 507, when sufficient force is applied thereto, during insertion and removal of core layer 501.

Except for the above-noted difference, percutaneous gas diffusion device 500 may be used in manner similar to that described above for percutaneous gas diffusion device 100.

Figure 6:
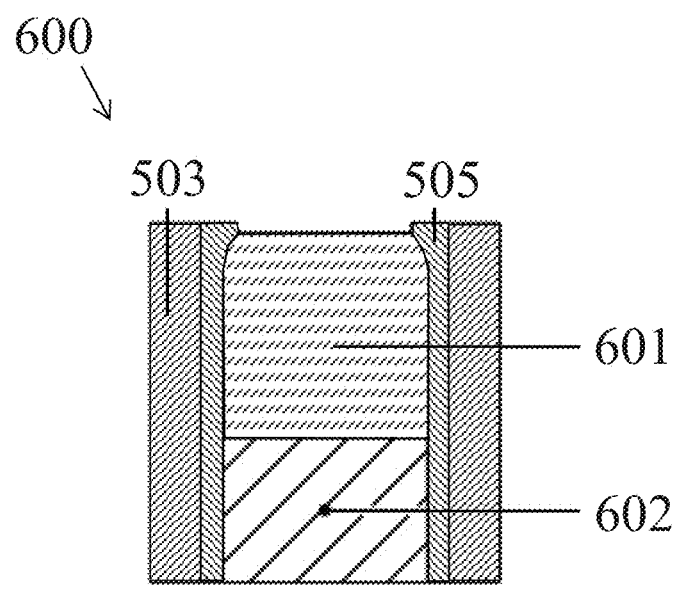
FIG. 6 is a section view of a fifth embodiment of a percutaneous gas diffusion device constructed according to the present invention for permitting the passage of one or more gases to and/or from an implant in a patient.

Referring now to FIG. 6, there is shown a section view of a fifth embodiment of a percutaneous gas diffusion device constructed according to the present invention for permitting the passage of one or more gases to and/or from an implant in a patient, the percutaneous gas diffusion device being represented generally by reference numeral 600.

Percutaneous gas diffusion device 600 may be similar in most respects to percutaneous gas diffusion device 500, the principal difference between the two devices being that, whereas percutaneous gas diffusion device 500 may comprise core layer 501, which may be a one-piece structure, percutaneous gas diffusion device 600 may comprise a two-piece core layer comprising a removable core layer portion 601 and a fixed core layer portion 602. Removable core layer portion 601 may be positioned towards the exterior of the patient's body, and fixed core layer portion 602 may be positioned towards the interior of the patient's body. Like core layer 501 of percutaneous gas diffusion device 500, removable core layer portion 601 may be removed, when desired, from its adjacent intermediate layer 505 and, thereafter, reinserted or replaced. Fixed core layer portion 602 may serve to prevent contamination of an implanted medical device when removable core layer portion 601 is removed.

Except for the above-noted difference, percutaneous gas diffusion device 600 may be used in manner similar to that described above for percutaneous gas diffusion device 500.

Figure 7:
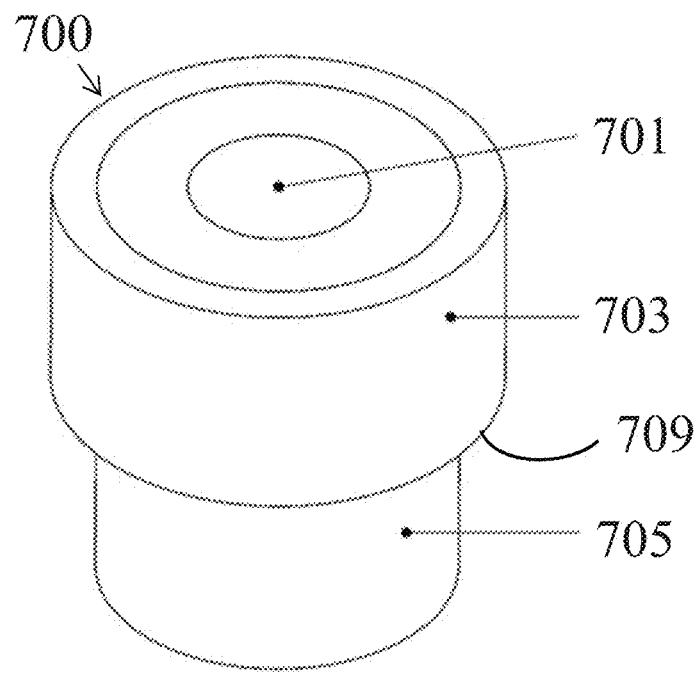
FIG. 7 is a perspective view of a sixth embodiment of a percutaneous gas diffusion device constructed according to the present invention for permitting the passage of one or more gases to and/or from an implant in a patient.
Figure 8:
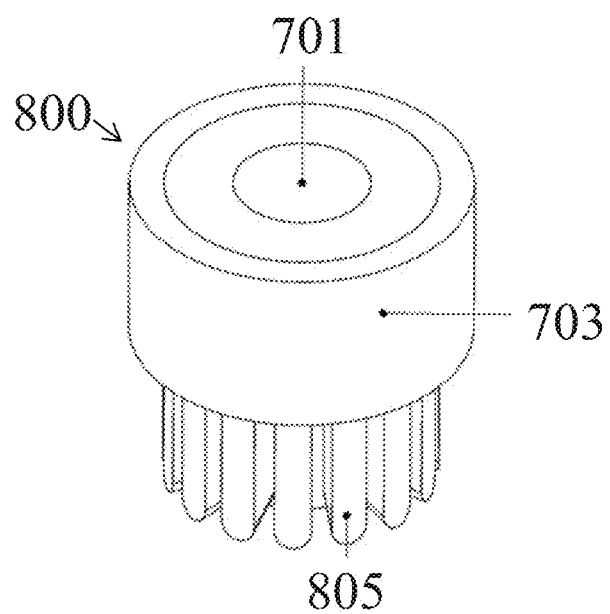
FIG. 8 is a perspective view of a seventh embodiment of a percutaneous gas diffusion device constructed according to the present invention for permitting the passage of one or more gases to and/or from an implant in a patient.
Figure 9:
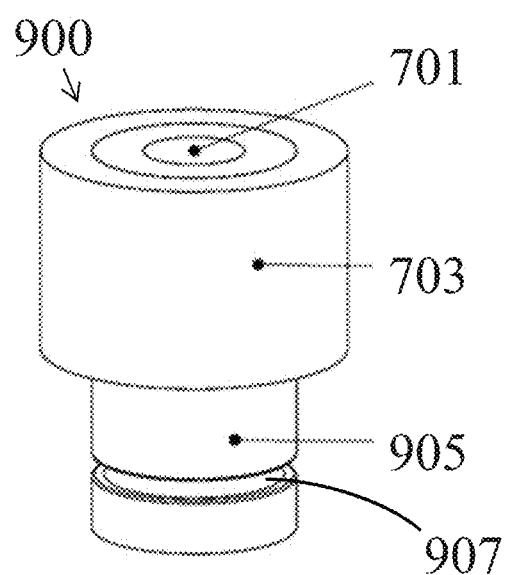
FIG. 9 is a perspective view of an eighth embodiment of a percutaneous gas diffusion device constructed according to the present invention for permitting the passage of one or more gases to and/or from an implant in a patient.

FIGS. 7 through 9 show various features that may be introduced into the percutaneous gas diffusion device of the present invention to enable a mechanically-strong, substantially gas-tight connection to an implant device, such as, but not limited to, a subcutaneous electrochemical gas generator or a container holding implanted cells and/or tissue. In each case, the core layer of the percutaneous gas diffusion device and/or the intermediate layer of the percutaneous gas diffusion device is extended beyond the outer layer of the percutaneous gas diffusion device so that the outer layer of the percutaneous gas diffusion device remains outside of an attached subcutaneous implant device while the extended sections enter the outer case of the attached subcutaneous implant device.

More specifically, referring now to FIG. 7, there is shown a view of a sixth embodiment of a percutaneous gas diffusion device constructed according to the present invention for permitting the passage of one or more gases to and/or from an implant in a patient, the percutaneous gas diffusion device being represented generally by reference numeral 700.

Percutaneous gas diffusion device 700 may be similar in most respects to percutaneous gas diffusion device 100 and may comprise a core layer 701 similar to core layer 101, an outer layer 703 similar to outer layer 103, and an intermediate layer 705 similar to intermediate layer 105. A principal difference between percutaneous gas diffusion device 700 and percutaneous gas diffusion device 100 may be that, whereas core layer 101, outer layer 103, and intermediate layer 105 of percutaneous gas diffusion device 100 all have the same length and have their respective top and bottom surfaces in alignment with one another, intermediate layer 705 of percutaneous gas diffusion device 700 (and, optionally, core layer 701) may extend downwardly beyond the bottom surface 709 of outer layer 703. In this manner, the exposed bottom portion of intermediate layer 705 may be mated to a complementarily-shaped portion of a subcutaneously-implanted device.

Except for the above-noted difference, percutaneous gas diffusion device 700 may be used in manner similar to that described above for percutaneous gas diffusion device 100.

Referring now to FIG. 8, there is shown a view of a seventh embodiment of a percutaneous gas diffusion device constructed according to the present invention for permitting the passage of one or more gases to and/or from an implant in a patient, the percutaneous gas diffusion device being represented generally by reference numeral 800.

Percutaneous gas diffusion device 800 may be similar in most respects to percutaneous gas diffusion device 700. A principal difference between percutaneous gas diffusion device 800 and percutaneous gas diffusion device 700 may be that, whereas intermediate layer 705 of percutaneous gas diffusion device 700 may have a smooth cylindrically-tubular shape, percutaneous gas diffusion device 800 may comprise an intermediate layer 805 comprising one or more ribs. Such a shape for intermediate layer 805 may facilitate connecting percutaneous gas diffusion device 800 to a subcutaneously-implanted medical device using a friction fit.

Except for the above-noted difference, percutaneous gas diffusion device 800 may be used in manner similar to that described above for percutaneous gas diffusion device 100.

Referring now to FIG. 9, there is shown a view of an eighth embodiment of a percutaneous gas diffusion device constructed according to the present invention for permitting the passage of one or more gases to and/or from an implant in a patient, the percutaneous gas diffusion device being represented generally by reference numeral 900.

Percutaneous gas diffusion device 900 may be similar in most respects to percutaneous gas diffusion device 700. A principal difference between percutaneous gas diffusion device 900 and percutaneous gas diffusion device 700 may be that percutaneous gas diffusion device 900 may comprise an intermediate layer 905 having a circumferential groove 907 whereas intermediate layer 705 of percutaneous gas diffusion device 700 may lack such a groove. Groove 907 may be used to enable intermediate layer 905 to engage with a fitting on a subcutaneously-implanted medical device.

Except for the above-noted difference, percutaneous gas diffusion device 900 may be used in manner similar to that described above for percutaneous gas diffusion device 100.

As can be appreciated, other features that would be apparent to those of ordinary skill in the art may be added to the core layer and/or the intermediate layer of any of the above-described embodiments to facilitate attachment of the percutaneous gas diffusion device to an implant device. Such features may include, but are not limited to, threads, flanges, and/or adhesives. If the core layer and/or the intermediate layer of the percutaneous gas diffusion device and the case of the implant device are formed from a metal, laser welding may be used to form a bond between the percutaneous gas diffusion device and the inside of the implant device case.

As noted above, the percutaneous gas diffusion device of the present invention is designed specifically to enable gas exchange between an implanted device, especially a subcutaneously implanted device, and air outside the body. The implanted device may be an electrochemical device for delivery of a therapeutic or supporting gas to a third device, such as a cell capsule, or directly to a location within the body. One such electrochemical device is an electrochemical oxygen concentrator (EOC). An EOC can be described as a hybrid cell combining an electrolysis anode and an air depolarized fuel cell cathode, with the anode and the cathode compartments separated by a relatively gas-impermeable solid polymer electrolyte membrane (PEM). The fundamental reactions that occur in an EOC are as follows:

$$2H_2O \rightarrow 4H^+ + 4e^- + O_2(pure)  \quad (1) \text{ Anode (Oxidation: loss of electrons):}$$

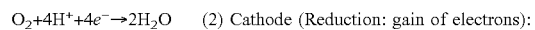
$$O_2 + 4H^+ + 4e^- \rightarrow 2H_2O \quad (2) \text{ Cathode (Reduction: gain of electrons):}$$

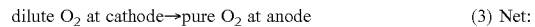
$$\text{dilute } O_2 \text{ at cathode} \rightarrow \text{pure } O_2 \text{ at anode} \quad (3) \text{ Net:}$$

In operation, the electrochemical cell acts as an oxygen concentrator by consuming oxygen at the cathode and collecting the pure oxygen generated at the anode. An EOC uses less energy than a classic electrolyzer and does not produce gaseous $H_2$.

Because an EOC acts as an oxygen concentrator, it requires access to oxygen in air at the cathode terminal. The percutaneous gas diffusion device of the present invention provides a path for oxygen from air outside the body to diffuse through the skin to the EOC with minimal risk of infection, and with minimal chance that contaminants will reach the interior of the EOC.

The EOC in the scenario described above is intended to deliver oxygen to cells inside the body. Those cells may be native cells or may be cells contained in a membrane-bound capsule. In some embodiments, a multi-chamber capsule may be used such that oxygen is delivered to a gas compartment and then diffuses across the walls of the gas compartment into one or more cell compartments, thus providing supplemental oxygen to the cell implant. Oxygen demand for encapsulated cellular implants may range between about 0.1 SCCH (standard cubic centimeters per hour) and 50 SCCH and may most preferably range between about 0.5 SCCH and 10 SCCH, depending on cell packing density in the capsule, cell mass, cell oxygen demand, and oxygen concentrations in the environment around the cell capsule. As can be appreciated, the permeability or porosity, and diameter of the gas-permeable core of the percutaneous gas diffusion device of the present invention should be chosen so that the flux of oxygen from the air through the percutaneous gas diffusion device matches the oxygen requirements of the cell implant. In other words, since the EOC is effectively an oxygen concentrator, rather than an oxygen generator, the design of the percutaneous gas diffusion device should allow diffusion or convection of oxygen through the skin that is at least equal to the volume of oxygen delivered by the EOC.

Figure 10A:
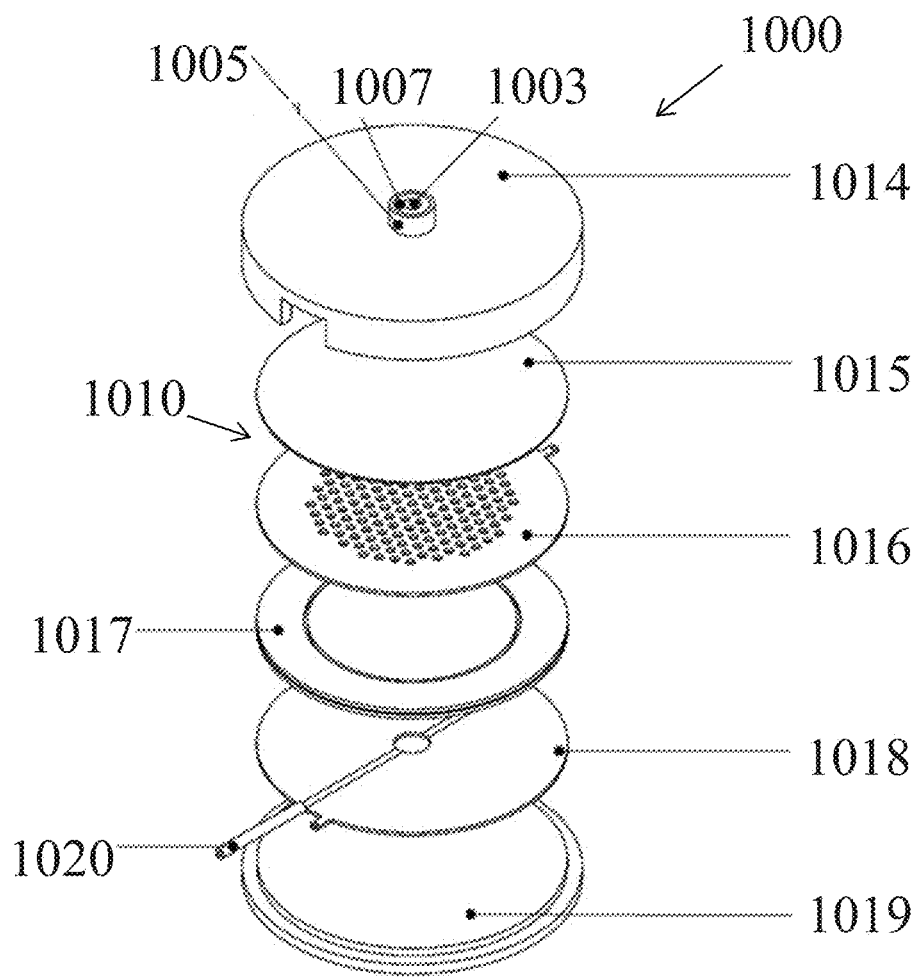
FIGS. 10A and 10B are partly exploded perspective and section views, respectively, of a second embodiment of an implant system constructed according to the present invention, the implant system comprising an electrochemical oxygen concentrator and the percutaneous gas diffusion device of FIG. 7, the percutaneous gas diffusion device being coupled to the cathode of the electrochemical oxygen concentrator so as to supply ambient air to the cathode of the electrochemical oxygen concentrator.
Figure 10B:
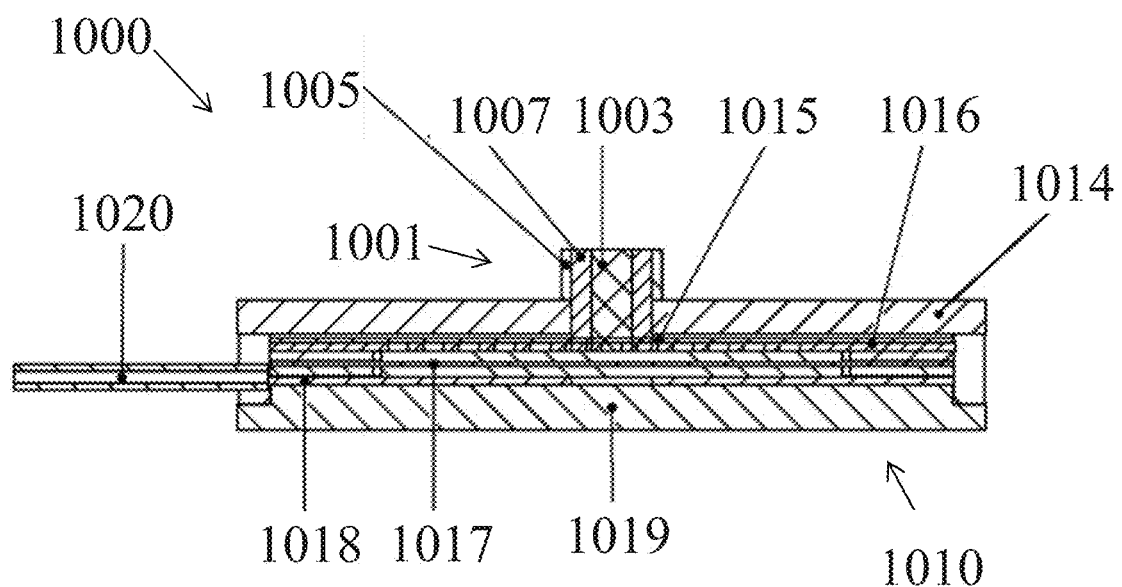

Referring now to FIGS. 10A and 10B, there are shown views of a second embodiment of an implant system constructed according to the present invention, the implant system being represented generally by reference numeral 1000. (For simplicity and clarity, certain components of implant system 1000 that are not critical to an understanding of the present invention are either not shown or described herein or are shown and/or described herein in a simplified manner.)

Implant system 1000 may comprise a percutaneous gas diffusion device 1001. Percutaneous gas diffusion device 1001 may be identical to percutaneous gas diffusion device 700 and may comprise a core layer 1003 identical to core layer 701, an outer layer 1005 identical to outer layer 703, and an intermediate layer 1007 identical to intermediate layer 705.

Implant system 1000 may further comprise an EOC 1010. EOC 1010, in turn, may comprise a top housing 1014, a hydrophobic membrane 1015, a cathode 1016, a membrane electrode assembly 1017, an anode 1018, and a bottom housing 1019.

Percutaneous gas diffusion device 1001 may be secured to top housing 1014. Top housing 1014 may be manufactured from any of a variety of materials. Preferred materials for top housing 1014 may include an implant-grade metal, such as titanium or stainless steel, a ceramic, and a plastic, such as polyether ether ketone (PEEK). Hydrophobic membrane 1015 may be positioned between percutaneous gas diffusion device 1001 and top housing 1014, and cathode 1016 as further protection of the electrochemical components from any contaminant that may penetrate percutaneous gas diffusion device 1001. Cathode 1016 may be placed in contact with membrane electrode assembly 1017, which catalyzes the anodic and cathodic reactions. An anode 1018 may be positioned between membrane electrode assembly 1017 and bottom housing 1019. Concentrated oxygen may be transported out of the EOC through a lumen or tube 1020 located near anode 1018 and that is attached to the EOC using standard mechanical means. As seen best in FIG. 10B, outer layer 1005 of percutaneous gas diffusion device 1001 extends only to the top surface of top housing 1014 while core layer 1003 and intermediate layer 1007 extend through to the bottom surface of top housing 1014. In this configuration, percutaneous gas diffusion device 1001 may be connected to top housing 104 using mechanical means, such as a friction fit or a laser weld, or by an adhesive.

Another example of an electrochemical device that can be paired with the percutaneous gas diffusion device of the present invention is a water electrolyzer. Implanted electrolyzers harvest water vapor from the body and generate separate oxygen and hydrogen gas streams. The gas that is generated can be delivered either to the body directly or may be delivered to a capsule that contains a cellular or tissue implant. Electrolyzers produce oxygen and hydrogen in a 1:2 molar ratio, respectively. If only one gas stream is required for treatment, it is advantageous to allow the unwanted gas to escape through the skin. This approach saves space that would otherwise be required for a system to safely deliver the waste gas to the body for eventual elimination.

Figure 11A:
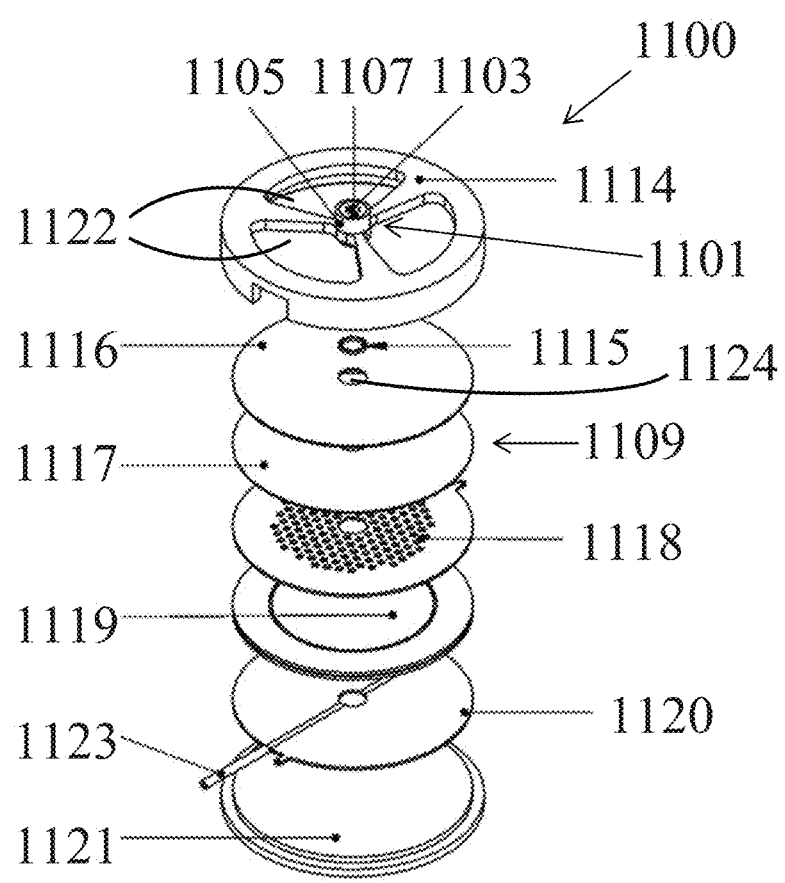
FIGS. 11A and 11B are partly exploded perspective and section views, respectively, of a third embodiment of an implant system constructed according to the present invention, the implant system comprising an electrolyzer and the percutaneous gas diffusion device of FIG. 9, the percutaneous gas diffusion device being coupled to the cathode of the electrolyzer so as to vent hydrogen through the percutaneous gas diffusion device.
Figure 11B:
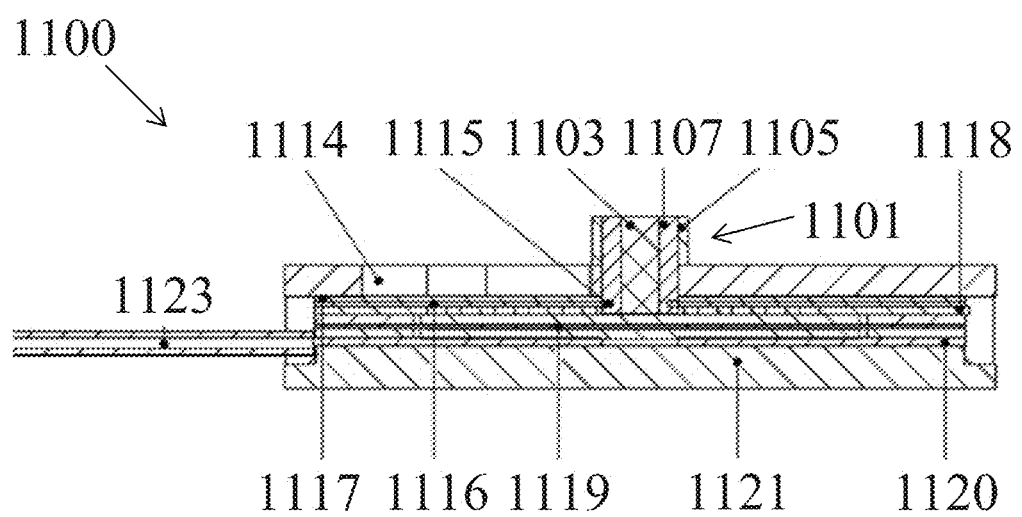

Referring now to FIGS. 11A and 11B, there are shown views of a third embodiment of an implant system constructed according to the present invention, the implant system being represented generally by reference numeral 1100. (For simplicity and clarity, certain components of implant system 1100 that are not critical to an understanding of the present invention are either not shown or described herein or are shown and/or described herein in a simplified manner.)

Implant system 1100 may comprise a percutaneous gas diffusion device 1101. Percutaneous gas diffusion device 1101 may be identical to percutaneous gas diffusion device 900 and may comprise a core layer 1103 identical to core layer 701, an outer layer 1105 identical to outer layer 703, and an intermediate layer 1107 identical to intermediate layer 905.

Implant system 1100 may further comprise an electrolyzer 1109 that is configured to deliver oxygen either to the body, or to a cell implant. Electrolyzer 1109, in turn, may comprise a top housing 1114, an O-ring 1115, a vascularizing membrane 1116, a hydrophobic membrane 1117, a cathode 1118, a membrane electrode assembly 1119, an anode 1120, and a bottom housing 1121.

Percutaneous gas diffusion device 1101 may be secured to top housing 1114, which may have openings 1122 to enable vascularizing membrane 1116 to come into contact with the tissue in the subcutaneous space. The structure of vascularizing membrane 1116 encourages growth of blood vessels close to the membrane surface and reduces the foreign body response. Hydrophobic membrane 1117 may be positioned between vascularizing membrane 1116 and cathode 1118 and may function to prevent non-volatile compounds from interacting with either cathode 1118 or membrane electrode assembly 1119. Oxygen produced at anode 1120 exits electrolyzer 1109 through a tube 1123 positioned near anode 1120 and that may be connected to the system using standard mechanical means. Bottom housing 1121 mates with top housing 1114 to seal the device. A hole 1124 may be provided in the center of vascularizing membrane 1116 to enable waste hydrogen generated at cathode 1118 to pass through core layer 1103 of percutaneous gas diffusion device 1101. O-ring 1115 forms a seal around hole 1124 in vascularizing membrane 1116. FIG. 11B shows more clearly that the outer layer 1105 of percutaneous gas diffusion device 1101 extends only to the upper surface of top housing 1114 while core layer 1103 and intermediate layer 1107 of percutaneous gas diffusion device 1101 extend through top housing 1114. Joining of the percutaneous gas diffusion device 1101 to electrolyzer 1109 may be achieved using mechanical means, such as a friction fit or a laser weld, or by an adhesive.

As can be appreciated, in implant system 1100, percutaneous gas diffusion device 1101 functions to enable hydrogen gas to leave the body. The water required for electrolysis enters through openings in the electrolyzer housing. A series of water vapor harvesting membranes protect the electrolyzer from nonvolatile compounds found in interstitial fluid and blood. Structural elements in top housing 1114 act both to maintain contact between cathode 1118 and membrane electrode assembly 1119 and to provide means to attach percutaneous gas diffusion device 1101 to top housing 1114.

Figure 12A:
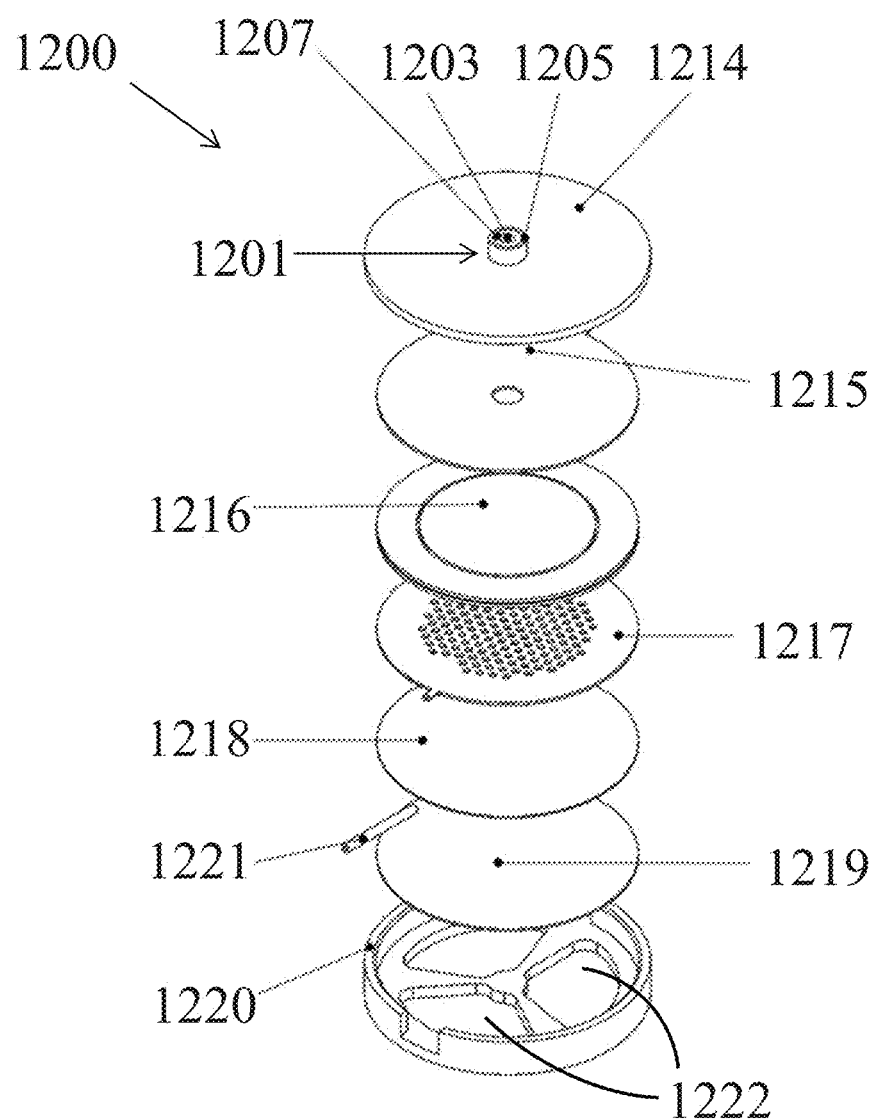
FIGS. 12A and 12B are partly exploded perspective and section views, respectively, of a fourth embodiment of an implant system constructed according to the present invention, the implant system comprising an electrolyzer and the percutaneous gas diffusion device of FIG. 9, the percutaneous gas diffusion device being coupled to the anode of the electrolyzer so as to vent oxygen through the percutaneous gas diffusion device.
Figure 12B:
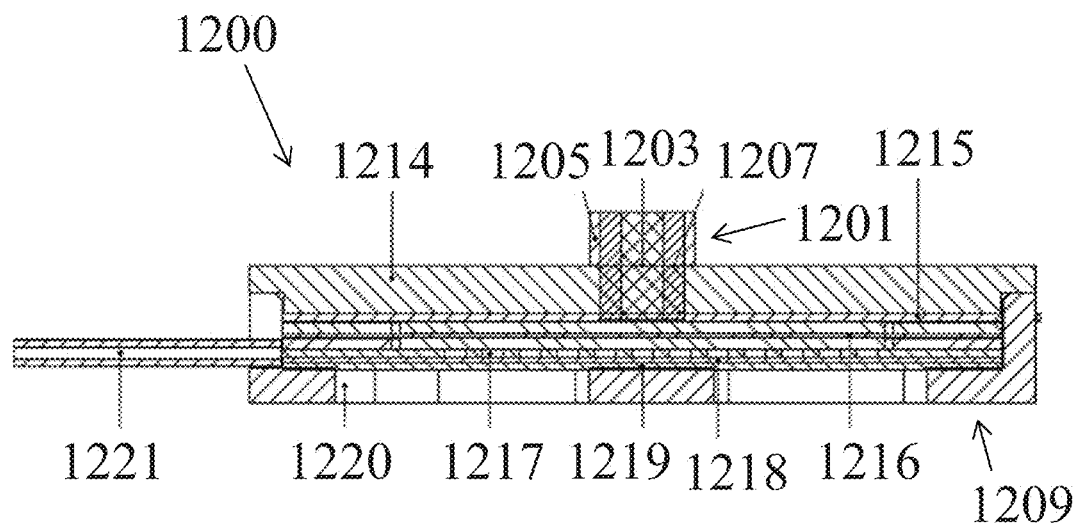

It may be desirable to deliver hydrogen to the body as part of a therapeutic regimen. In this case, the hydrogen generated by the electrolyzer will be transported to an implanted gas diffuser system, and the oxygen will be eliminated through the percutaneous gas diffusion device of the present invention. An example of such an implant system is depicted in FIGS. 12A and 12B and is represented generally by reference numeral 1200.

Implant system 1200 may comprise a percutaneous gas diffusion device 1201. Percutaneous gas diffusion device 1201 may be identical to percutaneous gas diffusion device 1101 and may comprise a core layer 1203 identical to core layer 701, an outer layer 1205 identical to outer layer 703, and an intermediate layer 1207 identical to intermediate layer 905.

Implant system 1200 may further comprise an electrolyzer (or EOG) 1209 that is configured to deliver hydrogen to the body. EOG 1209, in turn, may comprise a top housing 1214, an anode 1215, a membrane electrode assembly 1216, a cathode 1217, a hydrophobic membrane 1218, a vascularizing membrane 1219, and a bottom housing 1220.

Percutaneous gas diffusion device 1201 may be attached to top housing 1214. Membrane electrode assembly 1216 may be positioned between anode 1215 and cathode 1217. Hydrogen may be directed to a tube 1221 for delivery to an implanted gas diffuser, such as a network of permeable silicone tubing. It is preferable to have the water harvesting system on the cathode side of the electrochemical device. Bottom housing 1220 may feature openings 1222 to allow subcutaneous tissue to contact vascularizing membrane 1219. Hydrophobic membrane 1218 may ensure that nonvolatile materials are not able to contact anode 1215, cathode 1217, or membrane electrode assembly 1216. As seen best in FIG. 12B, outer layer 1205 of percutaneous gas diffusion device 1201 may extend only to the upper surface of top housing 1214 while core layer 1203 and intermediate layer 1207 of percutaneous gas diffusion device 1201 extend through top housing 1214. The joining of percutaneous gas diffusion device 1201 to the EOG may be achieved using mechanical means, such as a friction fit or a laser weld, or by an adhesive.

Figure 13:
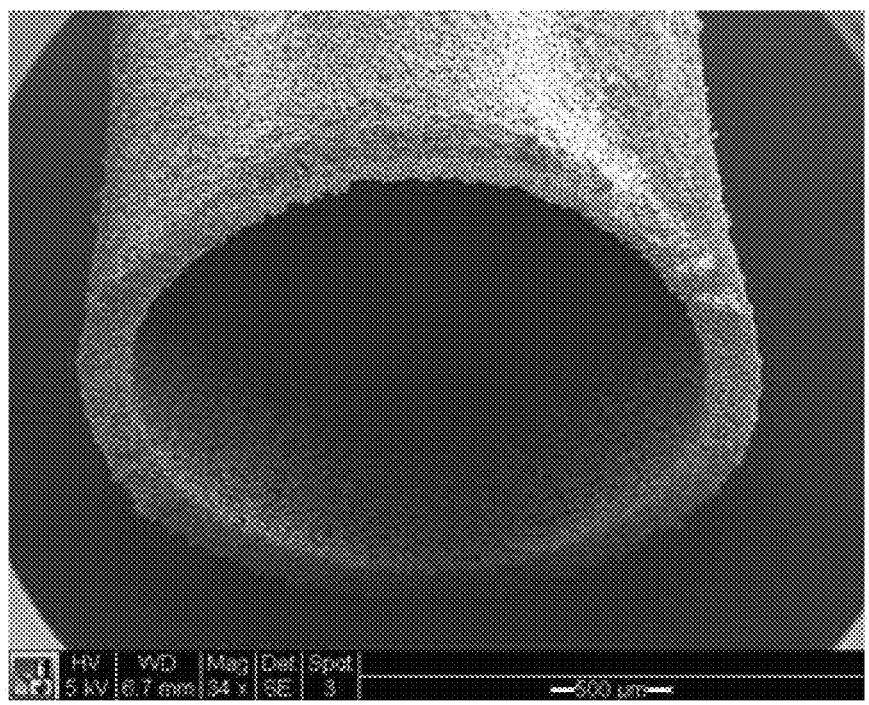
FIG. 13 is a scanning electron micrograph of a tube that may be used to form the tissue-integration layer of the percutaneous gas diffusion device of FIG. 1A.

FIG. 13 is a scanning electron micrograph of a tube that may be used as outer layer 103 of percutaneous gas diffusion device 100. This tube is fabricated from silicone STAR® biomaterial, a sphere-templated material (Healionics Corp., Seattle, Wash.) that features precise control of both void diameter and connecting pores. Approximate dimensions of the depicted material are illustrative and can be adjusted to meet the requirements of different applications: OD 2.7 mm; ID 2.4 mm; wall thickness 250 μm.

The following example is provided for illustrative purposes only and is in no way intended to limit the scope of the present invention:

Example 1: Demonstration of EOC Function Through a Gas-Permeable Core

Diffusion of sufficient oxygen through a gas-permeable core to generate a minimum of 1 SCCH (standard cubic centimeters per hour) $O_2$ was demonstrated using a laboratory EOC. POREX® BM50 sintered PTFE with a pore size of 3 μm (Porex Corporation, Fairburn, Ga.) was used as the gas-permeable core material for this experiment. The air inlet ports of the EOC were first covered with a 127 μm thick silicone membrane to protect the internal components of the EOC. The silicone was sufficiently oxygen-permeable to have no effect on performance. A 7 mm diameter, 2 mm high cylinder of POREX® material was attached to the silicone membrane above one inlet hole on the EOC. A skin simulant (ballistics gel: 12% gelatin in deionized water) was then cast over the surface of the EOC, leaving only the top of the POREX® material exposed.

Figure 14A:
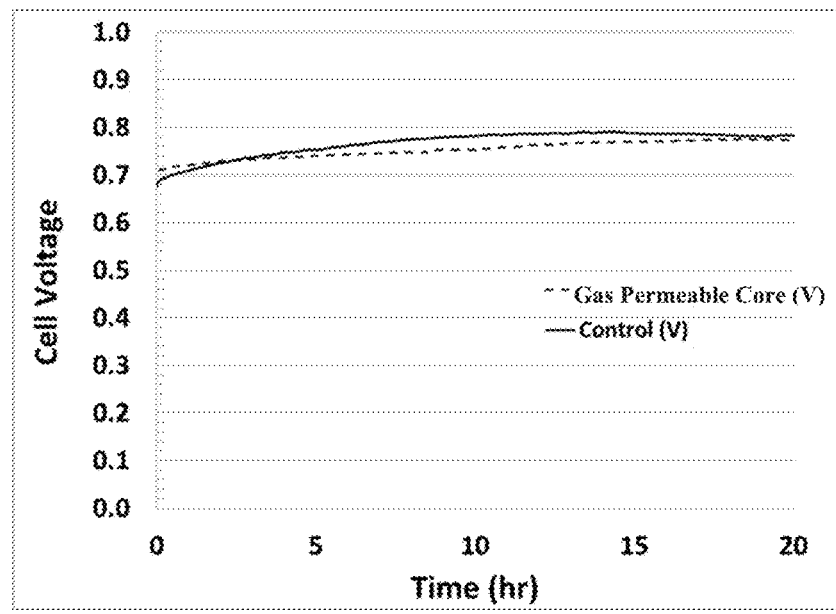
FIG. 14A is a graph, depicting cell voltage over time from an unmodified EOC (control) and for the same EOC with a gas-permeable core used as the only area for oxygen to diffuse to the EOC, as discussed in Example 1.
Figure 14B:
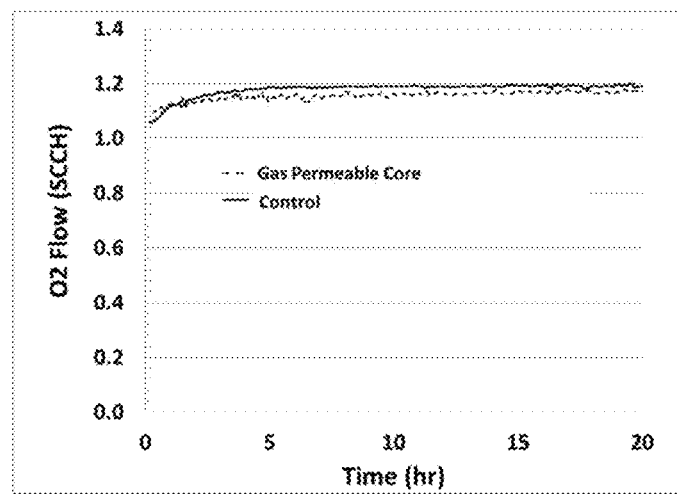
FIG. 14B is a graph, depicting oxygen flow over time from an unmodified EOC (control) and for the same EOC with a gas-permeable core used as the only area for oxygen to diffuse to the EOC, as discussed in Example 1.

The device was run for a minimum of 20 hours at 1.6 mA for each configuration. Voltage, an indicator of efficiency, peaked around 18 hours and remained stable at approximately 0.8 V for both configurations (FIG. 14A), which is within the acceptance criteria for the EOC. Oxygen flow for both configurations stabilized at approximately 1.2 SCCH (FIG. 14B). There was no significant difference in performance between the device with the gas-permeable core and the control. The stable voltage indicates that sufficient oxygen was available to the EOC via the gas-diffusion core even when all but the upper surface of the POREX® material was covered with the skin simulant.

The embodiments of the present invention described above are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A percutaneous gas diffusion device suitable for providing a percutaneous pathway for diffusion of one or more gases between an interior of a body and a location outside the body, the percutaneous gas diffusion device comprising:
   (a) a core layer, the core layer having a length, a top, a bottom, and a periphery, the core layer being gas-permeable and liquid-impermeable, the core layer being percutaneously positionable in the body so that the top of the core layer faces outside the body and the bottom of the core layer faces the interior of the body; and
   (b) an outer layer, the outer layer surrounding the periphery of the core layer for at least a portion of the length of the core layer, the outer layer comprising a tissue-integrating material.

2. The percutaneous gas diffusion device as claimed in claim 1 wherein the core layer has an open-pore structure.

3. The percutaneous gas diffusion device as claimed in claim 1 wherein the outer layer has a length and wherein the outer layer directly contacts the core layer over an entirety of the length of the outer layer that surrounds the periphery of the core layer.

4. The percutaneous gas diffusion device as claimed in claim 1 wherein the core layer has a closed-pore structure.

5. The percutaneous gas diffusion device as claimed in claim 1 wherein the core layer is a nonporous solid material.

6. The percutaneous gas diffusion device as claimed in claim 1 wherein the core layer comprises at least one material selected from the group consisting of porous polymers, non-porous gas-permeable materials, an open-cell ceramic foam, and a porous metal.

7. The percutaneous gas diffusion device as claimed in claim 6 wherein the at least one material of the core layer is treated with a hydrophobic polymer.

8. The percutaneous gas diffusion device as claimed in claim 1 wherein the core layer is cylindrical in shape.

9. The percutaneous gas diffusion device as claimed in claim 8 wherein the core layer has a diameter of no more than 5 mm and a length of 1.2-10 mm.

10. The percutaneous gas diffusion device as claimed in claim 9 wherein the core layer has a diameter of no more than 1 mm and a length of 2-5 mm.

11. The percutaneous gas diffusion device as claimed in claim 1 wherein the tissue-integrating material of the outer layer is at least one porous, biocompatible material selected from the group consisting of open-cell silicone foams, patterned microporous materials, open-cell urethane foams, sintered polymeric materials.

12. The percutaneous gas diffusion device as claimed in claim 1 wherein the outer layer has a thickness of 0.2-1.0 mm and a length of 1.2-2.0 mm.

13. The percutaneous gas diffusion device as claimed in claim 1 wherein the outer layer has a length and wherein the length of the outer layer matches the length of the core layer.

14. The percutaneous gas diffusion device as claimed in claim 1 wherein the outer layer has a bottom and wherein the bottom of the core extends downwardly beyond the bottom of the outer layer.

15. The percutaneous gas diffusion device as claimed in claim 1 wherein the core layer is fixedly coupled to the outer layer.

16. The percutaneous gas diffusion device as claimed in claim 1 wherein the core layer is removably coupled to the outer layer.

17. The percutaneous gas diffusion device as claimed in claim 1 wherein a portion of the core layer is fixedly coupled to the outer layer and a portion of the core layer is removably coupled to the outer layer.

18. The percutaneous gas diffusion device as claimed in claim 1 wherein at least a portion of the outer layer is spaced apart from the core layer to define a space that surrounds the core layer, the percutaneous gas diffusion device further comprising an intermediate layer, the intermediate layer being positioned between the core layer and the outer layer and completely filling the space between the core layer and the outer layer.

19. The percutaneous gas diffusion device as claimed in claim 18 wherein the intermediate layer comprises a barrier that prevents infiltration of tissue from the outer layer into the core layer.

20. The percutaneous gas diffusion device as claimed in claim 18 wherein the intermediate layer comprises a barrier that prevents infiltration of tissue from the outer layer into the core layer and that reduces diffusion of gas from the core layer into the outer layer.

21. The percutaneous gas diffusion device as claimed in claim 18 wherein the intermediate layer has a bottom, wherein the outer layer has a bottom, and wherein the bottom of the intermediate layer extends downwardly beyond the bottom of the outer layer.

22. The percutaneous gas diffusion device as claimed in claim 18 wherein at least one of the core layer and the intermediate layer is configured to permit the removable coupling of at least a portion of the core layer to the intermediate layer.

23. The percutaneous gas diffusion device as claimed in claim 22 wherein the core layer comprises at least one notch adapted for engagement with a tool.

24. The percutaneous gas diffusion device as claimed in claim 23 wherein the intermediate layer comprises at least one notch adapted for engagement with a tool.

25. The percutaneous gas diffusion device as claimed in claim 22 wherein the core layer and the intermediate layer have mating threads.

26. The percutaneous gas diffusion device as claimed in claim 22 wherein the intermediate layer comprises a bottom portion shaped for coupling to an implant device.

27. The percutaneous gas diffusion device as claimed in claim 26 wherein the bottom portion of the intermediate layer comprises at least one rib.

28. The percutaneous gas diffusion device as claimed in claim 26 wherein the bottom portion of the intermediate layer comprises a circumferential groove.

29. An implant system comprising:
(a) an implant device, the implant device being positionable in a body and comprising at least one of a gas inlet and a gas outlet;
(b) a percutaneous gas diffusion device suitable for providing a percutaneous pathway for diffusion of one or more gases between an interior of the body and a location outside the body, the percutaneous gas diffusion device being fluidically coupled to one of the gas inlet and the gas outlet of the implant device, the percutaneous gas diffusion device comprising
  i. a core layer, the core layer having a first end and a second end, the core layer being gas-permeable and liquid-impermeable, the core layer being percutaneously positionable in the body so that the first end of the core layer faces outside the body and the second end of the core layer faces the interior of the body; and
  ii. an outer layer, the outer layer surrounding a periphery of the core layer for at least a portion of a length of the core layer, the outer layer comprising a tissue-integrating material.

30. The implant system as claimed in claim 29 wherein the implant device is a subcutaneous container for holding at least one of implanted cells and implanted tissue, wherein the subcutaneous container comprises an oxygen inlet, and wherein the percutaneous gas diffusion device is fluidically coupled to the oxygen inlet.

31. The implant system as claimed in claim 29 wherein the implant device is a subcutaneous electrochemical oxygen concentrator, wherein the subcutaneous electrochemical oxygen concentrator comprises an air inlet, and wherein the percutaneous gas diffusion device is fluidically coupled to the air inlet.

32. The implant system as claimed in claim 29 wherein the implant device is a subcutaneous water electrolyzer, the subcutaneous water electrolyzer comprising an oxygen outlet and a hydrogen outlet.

33. The implant system as claimed in claim 32 wherein the percutaneous gas diffusion device is fluidically coupled to the oxygen outlet.

34. The implant system as claimed in claim 32 wherein the percutaneous gas diffusion device is fluidically coupled to the hydrogen outlet.

35. The implant system as claimed in claim 29 wherein the implant device is a subcutaneous electrochemical cell capable of alternatively operating in an electrochemical oxygen concentrator mode and an electrochemical oxygen generator mode.

36. A method comprising the steps of:
(a) providing the implant system of claim 35;
(b) implanting the implant system in a patient;
(c) then, operating the implant system in the electrochemical oxygen concentrator mode, whereby contaminants may contaminate the core layer of the percutaneous gas diffusion device; and
(d) then, optionally operating the implant system in the electrochemical oxygen generator mode to expel the contaminants from the core layer of the percutaneous gas diffusion device.

* * * * *